United States Patent
Sweitzer

(10) Patent No.: US 11,723,781 B2
(45) Date of Patent: Aug. 15, 2023

(54) IMPLANT EXTRACTOR

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 53 days.

(21) Appl. No.: 16/738,479

(22) Filed: Jan. 9, 2020

(65) Prior Publication Data

US 2020/0214853 A1     Jul. 9, 2020

Related U.S. Application Data

(60) Provisional application No. 62/909,995, filed on Oct. 3, 2019, provisional application No. 62/790,176, filed on Jan. 9, 2019.

(51) Int. Cl.
*A61F 2/46* (2006.01)

(52) U.S. Cl.
CPC .... *A61F 2/4603* (2013.01); *A61F 2002/4619* (2013.01); *A61F 2002/4622* (2013.01)

(58) Field of Classification Search
CPC ............ A61F 2/4603; A61F 2002/4619; A61F 2002/462; A61F 2002/4622; A61F 2002/4628

See application file for complete search history.

(56) References Cited

U.S. PATENT DOCUMENTS

| | | | |
|---|---|---|---|
| 8,657,833 B2 * | 2/2014 | Burgi | A61F 2/4607 606/99 |
| 8,998,906 B2 * | 4/2015 | Kirschman | A61B 17/7068 606/205 |
| 2003/0225408 A1 | 12/2003 | Nichols et al. | |
| 2006/0136067 A1 * | 6/2006 | Pendleton | A61F 2/461 623/20.34 |
| 2008/0172061 A1 * | 7/2008 | Ragbir | A61F 2/4603 606/99 |
| 2008/0221576 A1 * | 9/2008 | Keller | A61F 2/4607 606/62 |

(Continued)

FOREIGN PATENT DOCUMENTS

| | | |
|---|---|---|
| CN | 102579168 A | 7/2012 |
| JP | h105277142 | 10/1993 |

(Continued)

OTHER PUBLICATIONS

International Search Report dated Apr. 16, 2020 in International Application No. PCT/US2020/012897.

(Continued)

*Primary Examiner* — Matthew J Lawson
(74) *Attorney, Agent, or Firm* — Kim IP Law Group LLC

(57) ABSTRACT

An implant extractor that includes an elongated body having a proximal end for attachment to an extraction device, a first arm extending from the elongated body, and a second arm pivotably connected to the first arm. The second arm includes a moment arm for generating a torque about a distal end of the second arm. The implant extractor further includes a force applicator operatively connected to the first arm and the moment arm to apply a force to one or more of the first and second arms.

3 Claims, 33 Drawing Sheets

(56) References Cited

U.S. PATENT DOCUMENTS

| | | | | |
|---|---|---|---|---|
| 2009/0136067 A1* | 5/2009 | Silvestri | ............... | H04R 1/1041 |
| | | | | 381/309 |
| 2009/0240254 A1* | 9/2009 | Arnhold | .................. | A61F 2/461 |
| | | | | 606/99 |
| 2009/0270873 A1* | 10/2009 | Fabian | .................. | A61F 2/4425 |
| | | | | 606/99 |
| 2012/0190255 A1* | 7/2012 | Yamazaki | ............... | B63B 34/10 |
| | | | | 440/88 L |
| 2014/0207123 A1 | 7/2014 | Mueller | | |
| 2014/0316522 A1* | 10/2014 | Weiman | ................ | A61F 2/4611 |
| | | | | 623/17.16 |
| 2016/0270929 A1* | 9/2016 | Sweitzer | .................. | A61F 2/461 |

FOREIGN PATENT DOCUMENTS

| | | |
|---|---|---|
| JP | 2009050682 A | 3/2009 |
| WO | WO2020146606 A1 | 7/2020 |

OTHER PUBLICATIONS

Written Opinion dated Apr. 16, 2020 in International Application No. PCT/US2020/012897.
Japanese Office Action dated Oct. 28, 2022 in Japanese Patent Application No. 2021-536719.
Australian Examination Report 2 dated Oct. 28, 2022 in Australian Patent Application No. 2020206707.
Australian Examination Report 1 dated Nov. 23, 2021 in Australian Patent Application No. 2020206707.
Australian Examination Report 3 dated Nov. 10, 2022 in Australian Patent Application No. 2020206707.
Australian Examination Report 4 dated Nov. 16, 2022 in Australian Patent Application No. 2020206707.
India Examination Report dated Mar. 29, 2022 in Indian Patent Application No. 202117035589.
International Search Report and Written Opinion dated Apr. 16, 2020 in International Application No. PCT/US2020/012897.

* cited by examiner

IMPLANT EXTRACTOR

CROSS-REFERENCE TO RELATED APPLICATIONS

The present application claims the benefit of U.S. Provisional Application No. 62/790,176, filed Jan. 9, 2019 and U.S. Provisional Application No. 62/909,995, filed Oct. 3, 2019, each of these prior-filed provisional applications being hereby incorporated by reference in their entirety as if part of the present disclosure.

BACKGROUND OF THE DISCLOSURE

The exemplary embodiments of the subject disclosure relate generally to a surgical extraction tool and, more specifically, to a tool for extracting an implant from bone.

SUMMARY OF THE DISCLOSURE

In accordance with an exemplary embodiment, the subject disclosure provides an implant extractor that includes an elongated body having a proximal end for attachment to an extraction device, a first arm extending from the elongated body, and a second arm pivotably connected to the first arm. The second arm includes a moment arm for generating a torque about a distal end of the second arm. The implant extractor further includes a force applicator operatively connected to the first arm and the moment arm to apply a force to one of the first and second arms.

In an exemplary embodiment, the first arm is integrally formed with the elongated body. In one embodiment, the first arm includes a first arm segment, and a second arm segment. The second arm segment can extend from the first arm segment and/or have a longitudinal axis at an angle of about 80° to about 160° relative to a longitudinal axis of the first arm segment. The first arm can further include a tail end extending laterally of first and second arm segments.

In another exemplary embodiment, the proximal end of the second arm is positioned directly above the tail end of the first arm. In one embodiment, the second arm further includes a distal arm segment having a longitudinal axis of about 80° to about 160° relative to a longitudinal axis of the moment arm. In one embodiment, one of the first arm and second arm extends through the other of the first arm and second arm.

In an exemplary embodiment, the force applicator includes a screw displacement device. In one embodiment, the screw displacement device includes a longitudinal axis substantially parallel to a longitudinal axis of the elongated body.

In another exemplary embodiment, the implant extractor includes a first jaw releasably attachable to a distal end of the first arm, and a second jaw releasably attachable to the distal end of the second arm. In one embodiment, a latch is provided for releasably retaining the first jaw to the distal end of the first arm or the second jaw to the distal end of the second arm. In one embodiment, a distal portion of at least one of the first and second jaws is substantially cup-shaped, substantially cylinder-shaped, substantially prong-shaped, substantially toothed-shaped, substantially conical, substantially J-shaped, substantially boot-shaped, substantially curved, or substantially dog-leg in shape.

In an exemplary embodiment, the elongated body includes an attachment mechanism to attach to an extraction device. In certain embodiments, the attachment mechanism can include a quick connect and/or a polygonal shaped base for attachment with a cooperating striking member.

BRIEF DESCRIPTION OF THE SEVERAL VIEWS OF THE DRAWINGS

The following detailed description of the exemplary embodiments of the subject disclosure will be better understood when read in conjunction with the appended drawings. For the purpose of illustrating the present disclosure, there is shown in the drawings exemplary embodiments. It should be understood, however, that the subject application is not limited to the precise arrangements and instrumentalities shown.

DETAILED DESCRIPTION OF THE DISCLOSURE

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1:
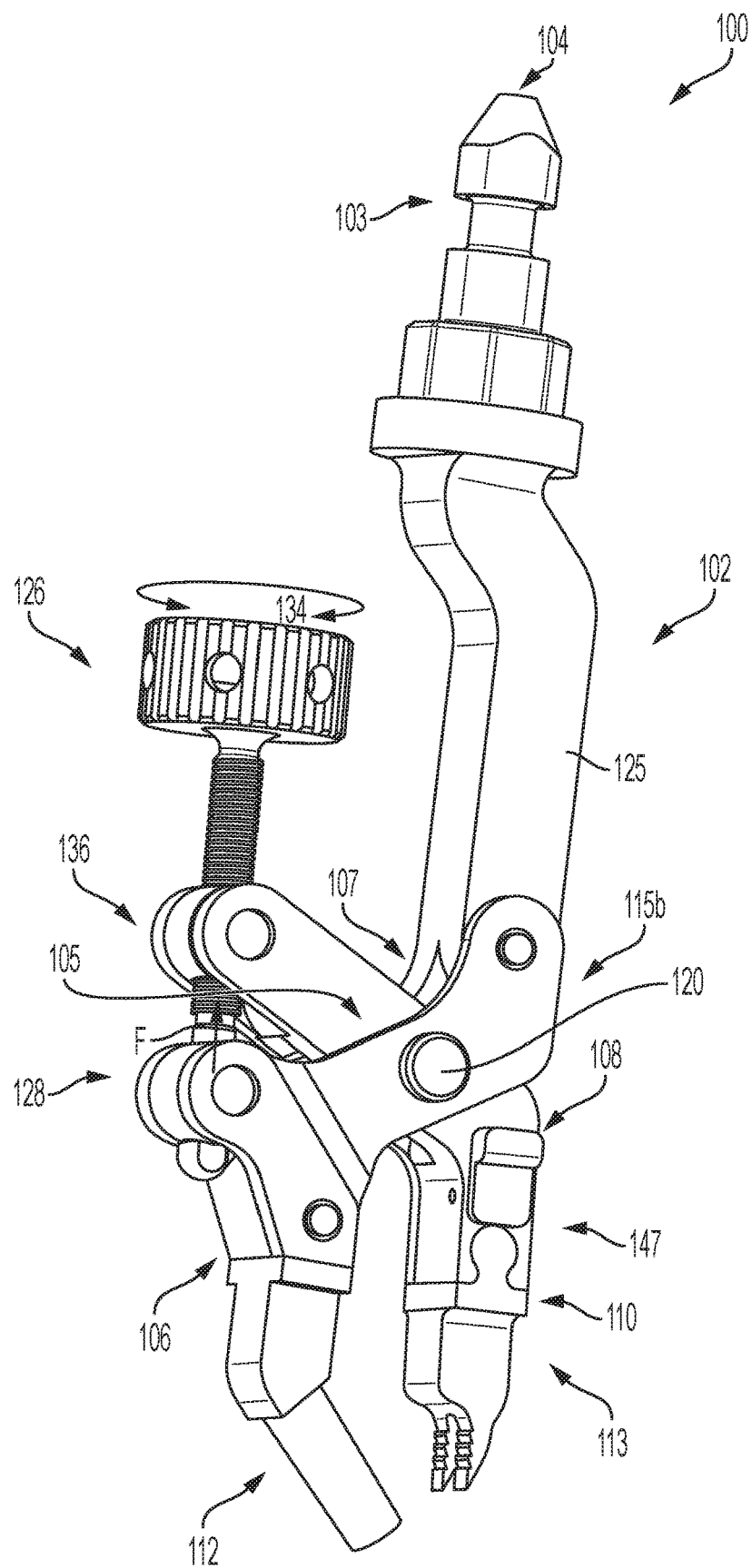
FIG. 1 is a front perspective view of an implant extractor in accordance with an exemplary embodiment of the subject disclosure.
Figure 2:
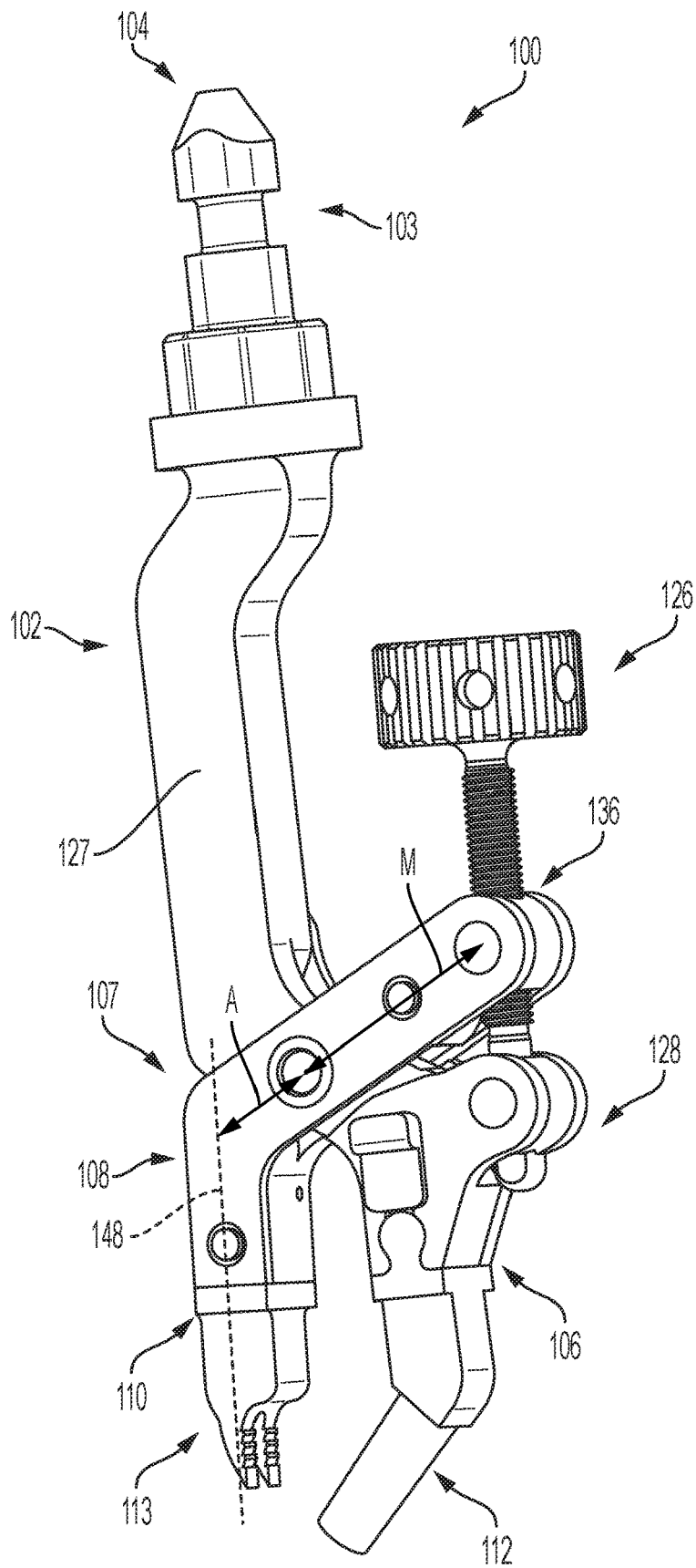
FIG. 2 is a rear perspective view of the implant extractor of FIG. 1.

Referring now to the drawings, FIGS. 1 and 2 illustrate an implant extractor 100 in accordance with an exemplary embodiment of the present disclosure. The implant extractor 100 comprises an elongated body 102 having an attachment mechanism 103 for attachment to an extraction device 101 about a proximal end 104 of the elongated body 102. The extraction device can include, without limitation, one or more of a T-handle extraction device 101 (FIGS. 20 and 21), a striking member 193 (FIG. 22) or any other extraction device capable of applying an extraction force to the implant extractor 100.

Figure 3:
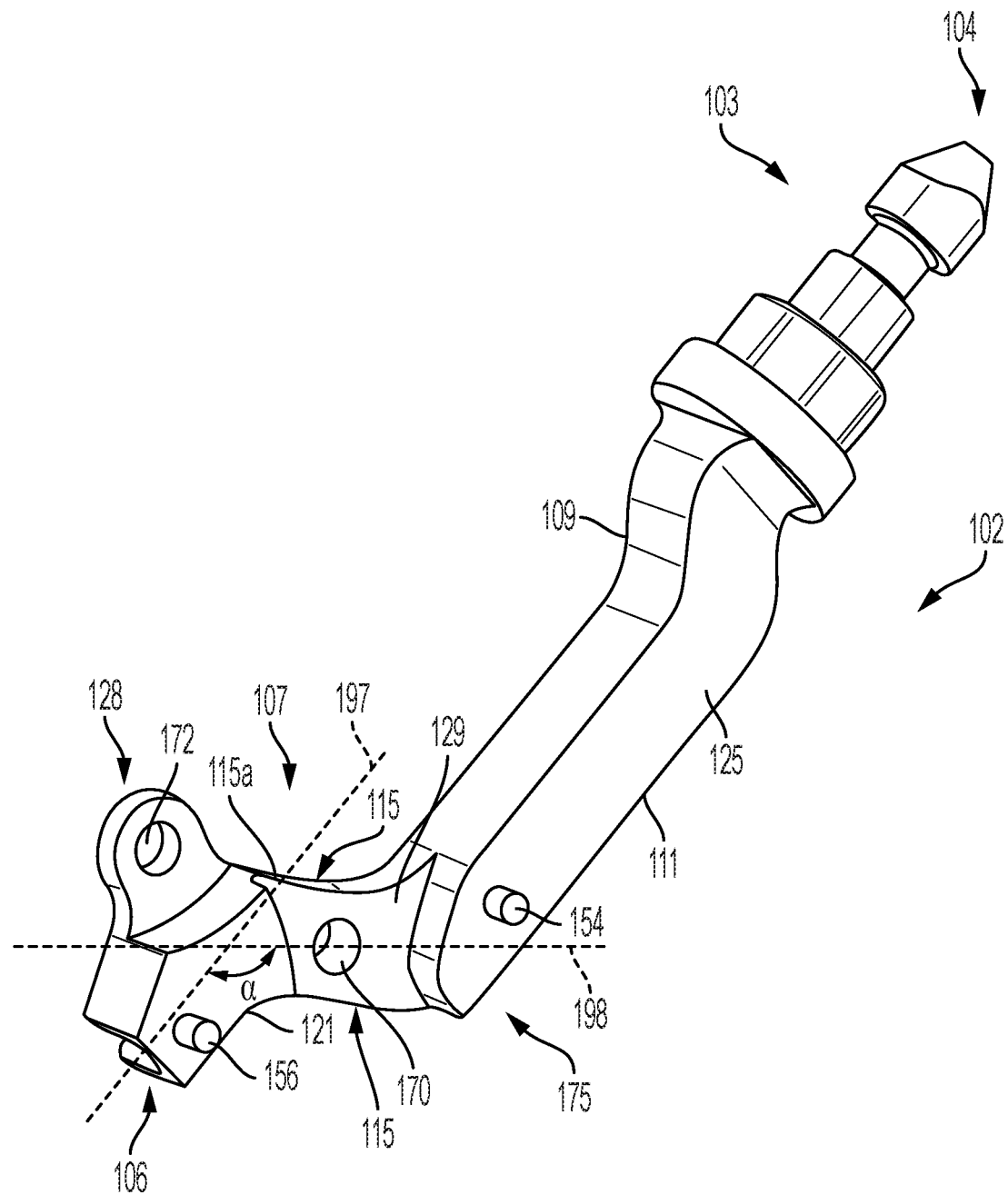
FIG. 3 is a front perspective view of an elongated body and first arm of the implant extractor of FIG. 1.

With reference to FIG. 3, the elongated body 102 has a distal end 175 opposite the proximal end 104. A first arm 107 extends from the elongated body 102. As will be discussed in greater detail below, in this particular embodiment, at least a portion of the first arm 107 is integrally formed with the elongated body 102 (see, e.g., FIGS. 2 and 3). Thus, in this particular embodiment, the elongated body is integrally formed with a portion of the first arm. Alternatively, the first arm 107 and the elongated body 102 can be provided as completely separate components that can be connected together e.g., in a rigid or pivotable connection.

A second arm 108 is pivotably connected to the first arm 107. The second arm 108 includes a moment arm 105 for generating a torque about a distal end 110 of the second arm 108. A force applicator 126 is operatively connected to the first arm 107 and the moment arm 105 of the second arm 108 to apply a force to one of the first and second arms.

A first jaw 112 is releasably attachable to the distal end 106 of the first arm 107 and a second jaw 113 is releasably attachable to the distal end 110 of the second arm 108. The first jaw 112 and second jaw 113 are modular and capable of being interchanged based on, for example, the shape of the implant to be extracted and the particular revision surgery being performed. Exemplary first and second jaws 112a-h, 113a-h according to particular exemplary embodiments are set forth in FIGS. 23-33 and are discussed in greater detail below, though aspects of the present disclosure are not limited to particular configurations shown therein.

Figure 4:
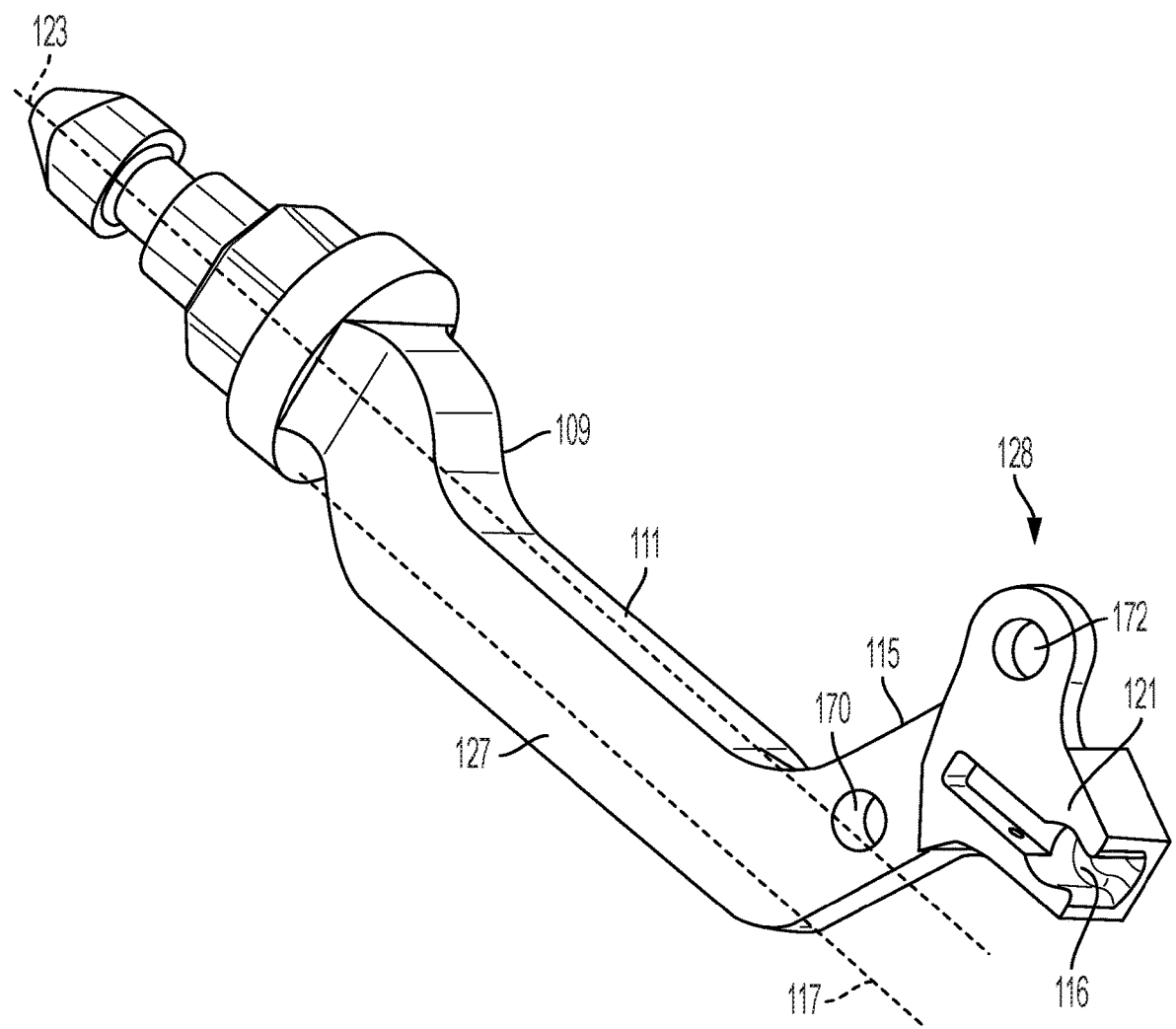
FIG. 4 is a rear perspective view of the elongated body and first arm of FIG. 3.
Figure 5:
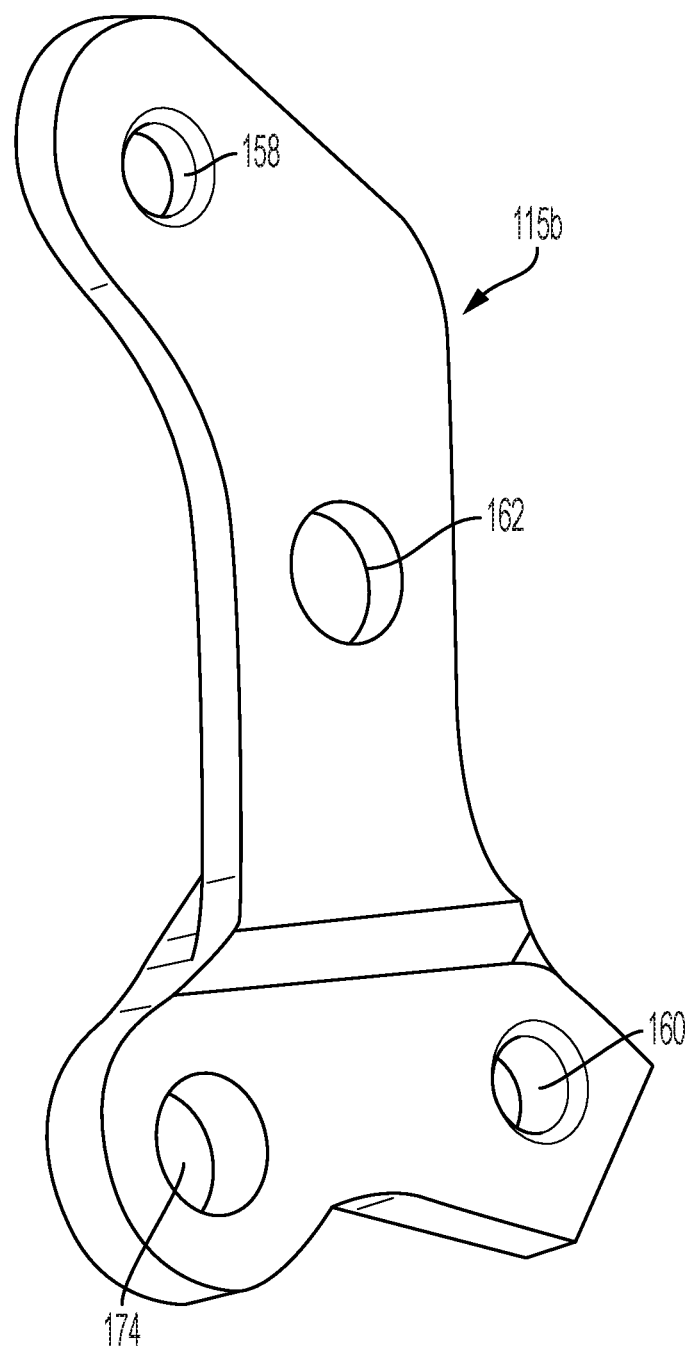
FIG. 5 is a perspective view of an outer surface of a first arm plate of the implant extractor of FIG. 1.
Figure 6:
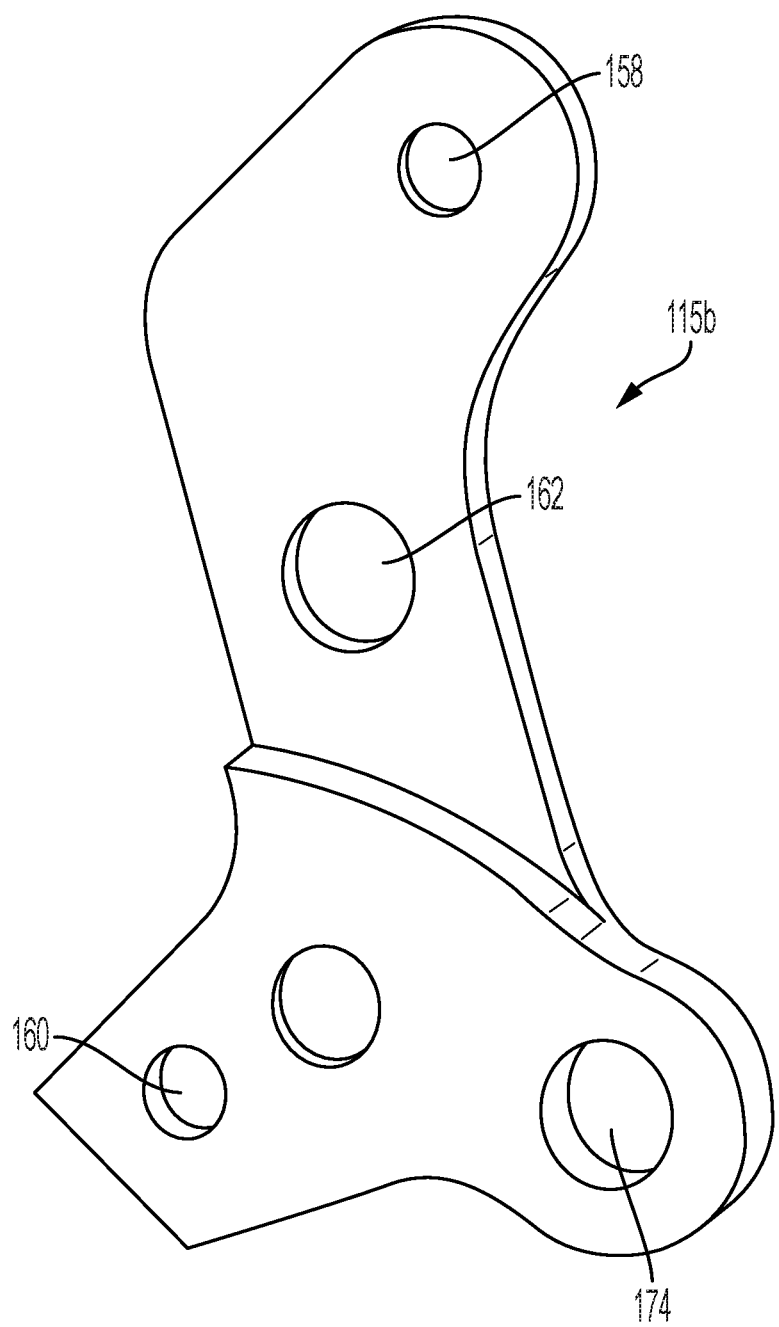
FIG. 6 is another perspective view of an inner surface of the first arm plate of FIG. 5.

The elongated body 102 has the first arm 107 extending therefrom, as shown in isolated detail in FIGS. 3-10, with a front side 125 shown in FIG. 3 and a back side 127 shown in FIG. 4. An attachment mechanism 103 is provided about and/or adjacent to the proximal end 104 of the elongated body 102. As will be discussed in greater detail below in connection with FIGS. 17-19, the attachment mechanism can include a quick connect.

With reference to FIGS. 3 and 4, the elongated body 102 has a proximal end 104 and a distal end 175. More particularly, the elongated body curves outwardly at a bend 109 (e.g., a S-shaped bend) from a central axis 123 of the attachment mechanism 103 to a main body 111 of the elongated body 102. This main body 111 defines a longitudinal axis 117 of the elongated body 102 that is laterally offset from the central axis 123 of the attachment mechanism owing to the bend 109.

A first arm segment 115 extends from the distal end 175 of the elongated body and curves inwardly or laterally from the main body 111 terminating toward an end 128 at a position further laterally than the central axis 123 of the attachment mechanism 103. The first arm curves laterally in the same direction the longitudinal axis of the attachment mechanism is laterally offset from the longitudinal axis of the main body. The first arm 107 includes a right arm 115a and a left arm 115b that collectively form the first arm. The first arm is also defined by a first arm segment 115 (or proximal end segment) and a second arm segment 121 (or distal arm segment).

As shown in FIG. 3, the first arm segment 115 defines a center longitudinal axis 197 and the second arm segment 121 defines a center longitudinal axis 198. The second arm segment 121 of the first arm 107 extends from the first arm segment 115 at an angle, α, distally from the first arm segment 115. The second arm segment 121 of the first arm defines a center longitudinal axis 198. The aforementioned angle, α, between longitudinal axis 197 and longitudinal axis 198 can range in certain exemplary embodiments from about 10° to about 170°, or from about 80° to about 160°, or from about 90° to about 150°, or from about 100° to about 140° (e.g., 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°.

A tail end 128 of the first arm 107 extends laterally from both the first arm segment 115 and the second arm segment 121 of the first arm 107. In other words, the tail end 128 is the lateral most end of the implant extractor from the elongated body 102.

Referring back to FIG. 3, an outwardly projecting pin 154 is provided along the main body 111 of the elongated body along the front side 125, and a second outwardly projecting pin 156 is provided along the second arm segment 121 of the first arm 107 along its front side 125. A through hole 170 is also provided between projecting pins 154 and 156 along the longitudinal axis 198 of the first arm segment 115. A second through hole 172 is provided near the tail end 128 of the first arm 107.

A left arm or plate 115b of the first arm 107 (FIGS. 5-7) is secured to the right arm 115a, and has an overall profile that corresponds in shape to the right arm 115a. A pair of through holes 158, 160 are provided in the plate 115b, respectively located about a proximal and a distal end of the plate. The through holes are shaped to receive the outwardly projecting pins 154, 156 on the elongated body 102 and right arm 115a. Situated between through holes 158, 160 in the plate 115b is another through hole 162 configured to receive a pivot shaft 164, as shown best in FIG. 9. As will be explained below, the pivot shaft 154 defines a joint 120 between the first arm 107 and the second arm 108. Another through hole 174 is provided in a position corresponding to the second through hole 172 about the tail end 128 of the right arm 115a.

Figure 7:
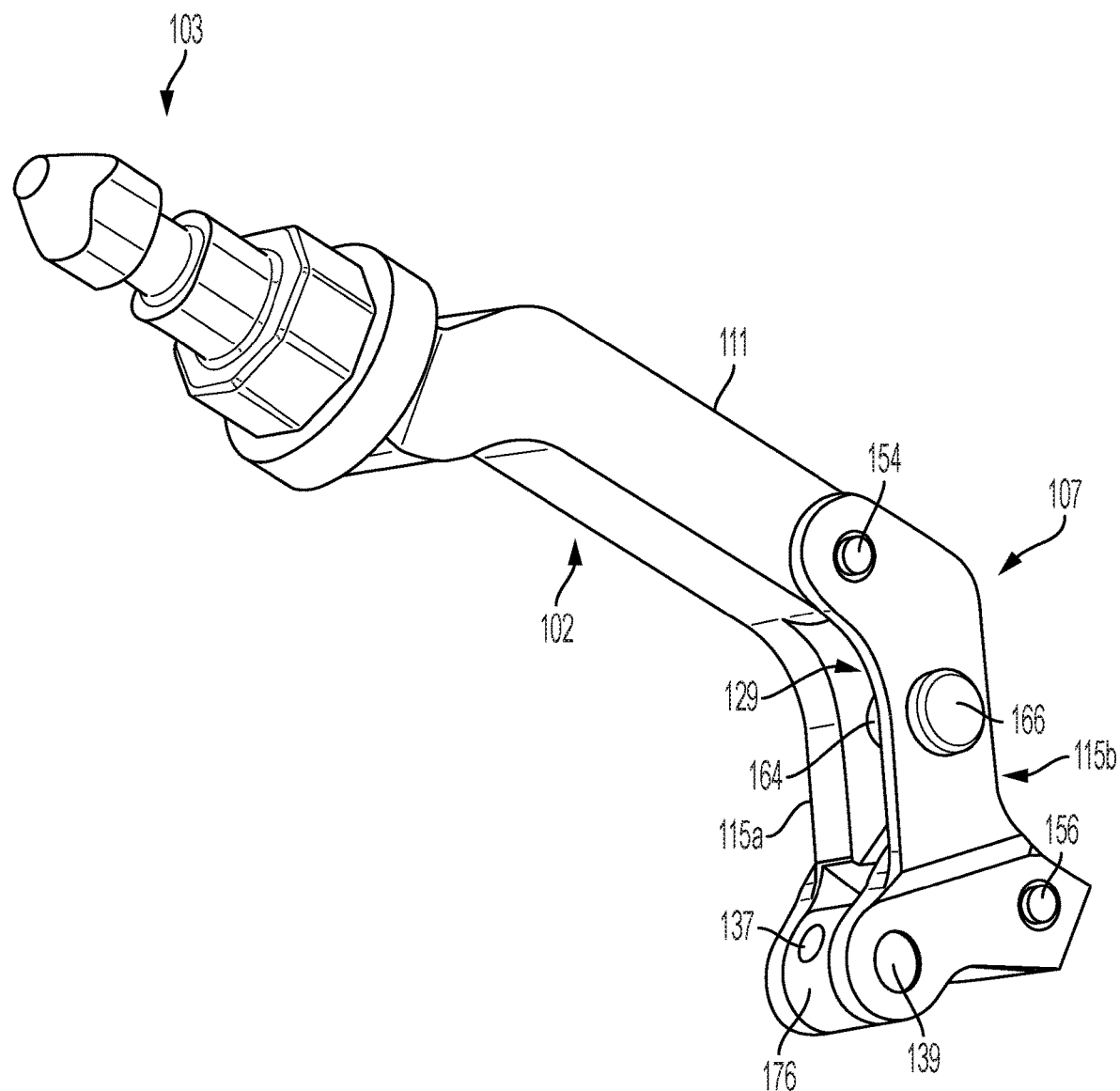
FIG. 7 is a front perspective view of the elongated body and first arm assembly of the implant extractor of FIG. 1.
Figure 8:
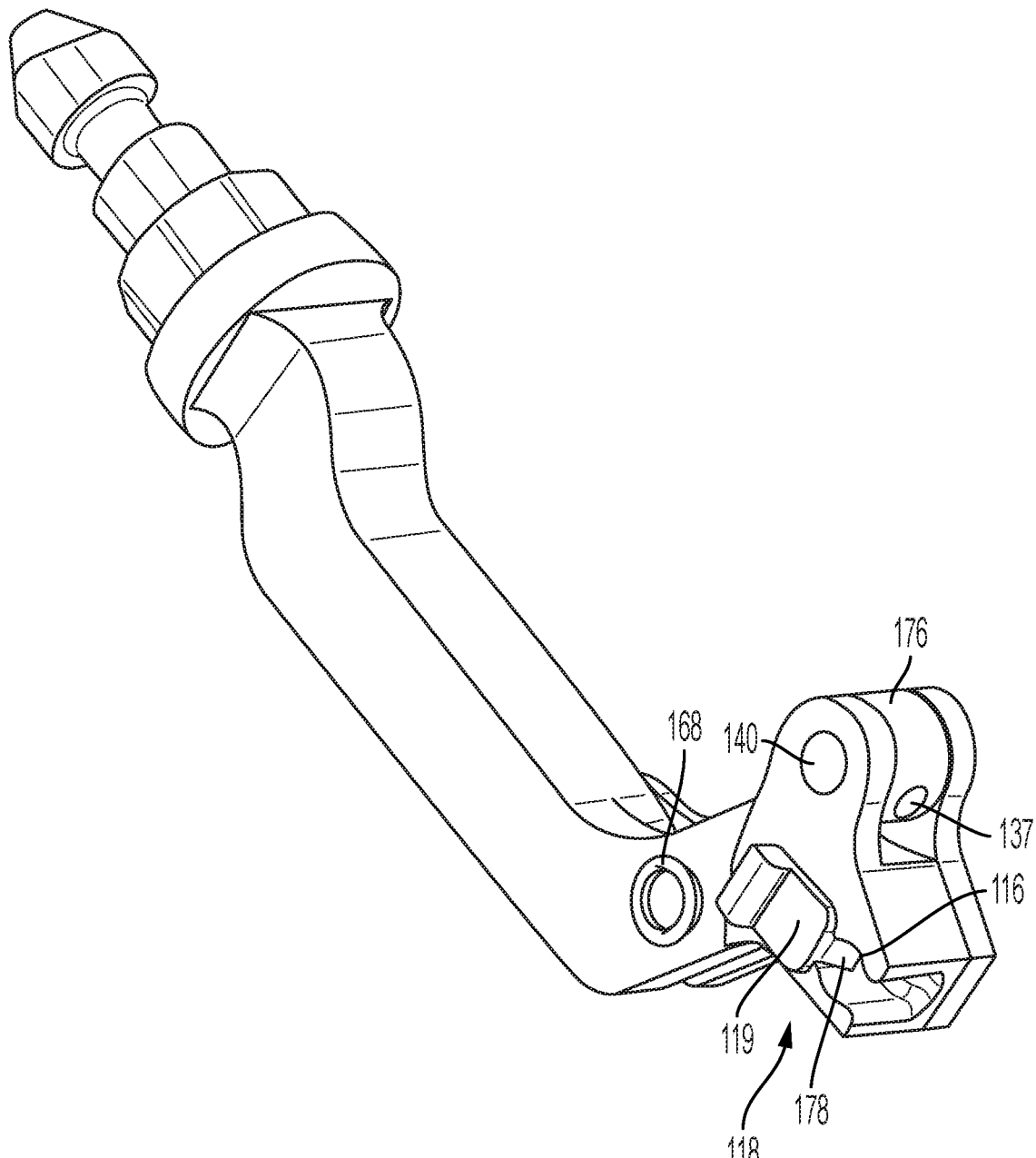
FIG. 8 is a rear perspective view of the elongated body and first arm of FIG. 7.

FIGS. 7-8 depict the first arm 107 fully assembled with the elongated body 102. As assembled, a recess 129 is provided between the right and left arms of the first arm 107 to allow passage and movement of the second arm 108 therethough. The pivot shaft 164 traverses the recess 129. The pivot shaft 164 has a first enlarged end 166 (FIG. 7) for securing the plate 115b and a second enlarged end 168 (FIG. 8) for retaining a right arm segment 108a of the second arm 108. Thus, as assembled, the second arm 108 extends through the first arm 107 about pivot shaft 164.

Referring to FIG. 8, a cross-member 176 is positioned towards or at the tail end 128 of the first arm 107. The cross-member 176 includes oppositely faced pins 139, 140 that are received by through hole 172 of the right arm 115a and through hole 174 of the plate 115b. The cross-member includes an orifice 137 shaped to receive a shaft, e.g., a recessed, non-threaded portion 133 of a shaft 135 of the force applicator 126, described in greater detail below.

Figure 9:
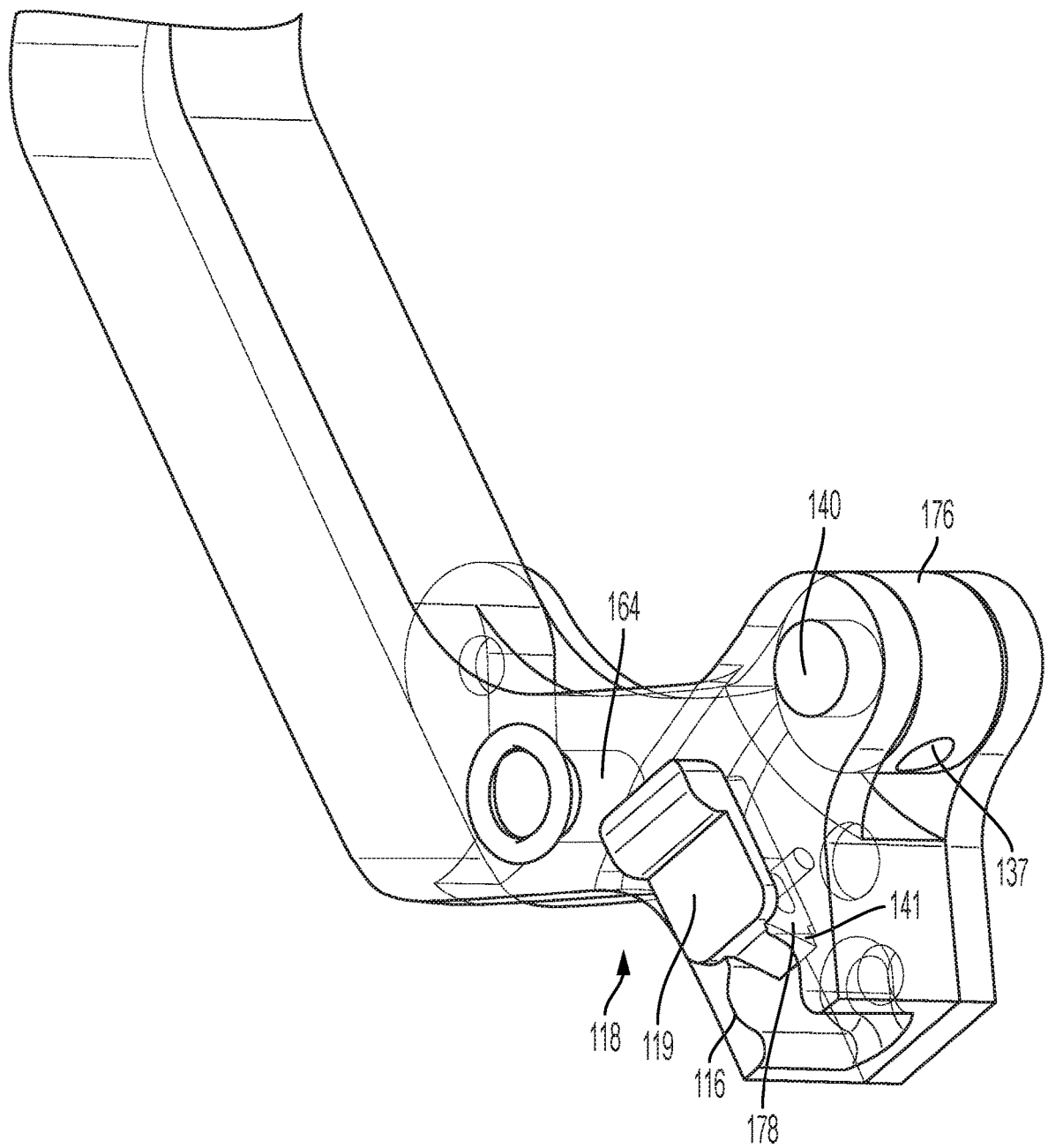
FIG. 9 is an enlarged partial perspective view of FIG. 8 with certain portions shown in phantom for purposes of illustration.

The distal end 106 of the first arm 107 includes a first socket 116 for releasably receiving a proximal end of the first jaw 112 and a first latch 118 for releasably securing the first jaw thereto. FIG. 9 shows an enlarged view of the first latch 118 for releasably securing a first jaw 112 to the first socket 116.

In this exemplary embodiment, the first latch 116 includes a slidable actuator 119 moveable between first and second latching and unlatching positions to lock and unlock the first jaw 112 in position within the first socket 116. The slidable actuator 119 is operatively engaged with a biased latch member 178 to allow the latch member to be moved against the bias of a biasing member (not shown). In this particular embodiment, the slidable actuator 119 has a back side to which the latch member 178 is fixedly connected.

The latch member 178 releasably engages with a notch 179 provided on a proximal end 177 of the first jaw 112 (FIGS. 23-32) to releasably retain the first jaw 112 to the first socket 116. As shown best in FIG. 9, the latch member 178 is shaped to contain a projecting notch 141 that is biased to fit inside the complimentarily shaped female notch 179 of the first jaw. Other latch configurations can be provided to releasably retain the jaw in accordance with the subject disclosure.

Figure 14:
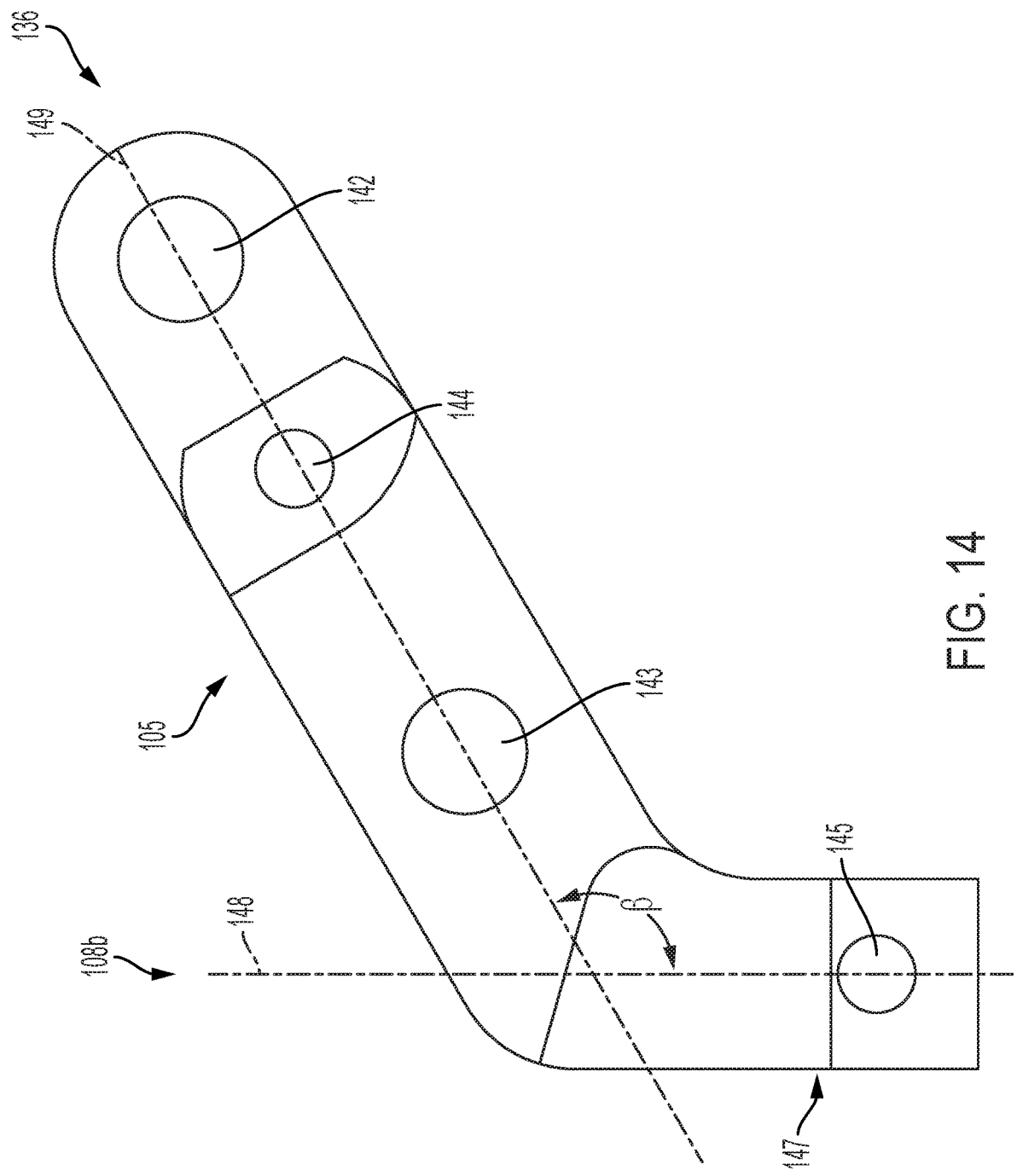
FIG. 14 is an isolated front view of an inner surface of the second arm of FIG. 13.

FIGS. 1, 2 and 10-15 show an exemplary structure of the second arm 108. The second arm 108 is formed from a right arm segment 108a and a left arm segment 108b and collectively forms a bent second arm 108. The second arm 108 has a first section that defines the moment arm 105 and a distal arm segment 147. The moment arm 105 is defined to be that part of the first section from its proximal end 136 to a through hole 143 about which the second arm is pivotably connected to the first arm. Referring to FIG. 14, a center longitudinal axis 148 of the distal arm segment extends at an angle, β, of from about 10° to about 180°, or from about 80° to about 160°, or from about 90° to about 150°, or from about 100° to about 140° (e.g., 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, relative to a center longitudinal axis 149 of the moment arm 105 or first section.

Figure 10:
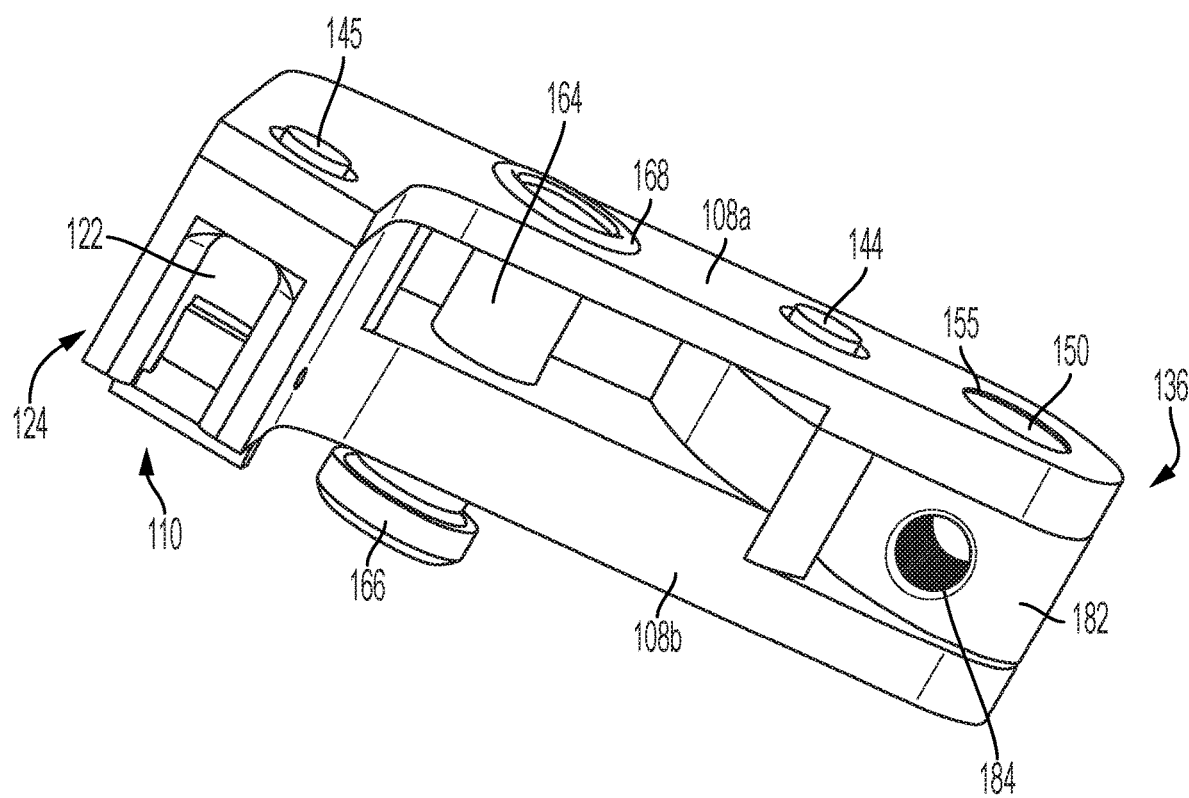
FIG. 10 is a bottom perspective view of a second arm of the implant extractor of FIG. 1.
Figure 11:
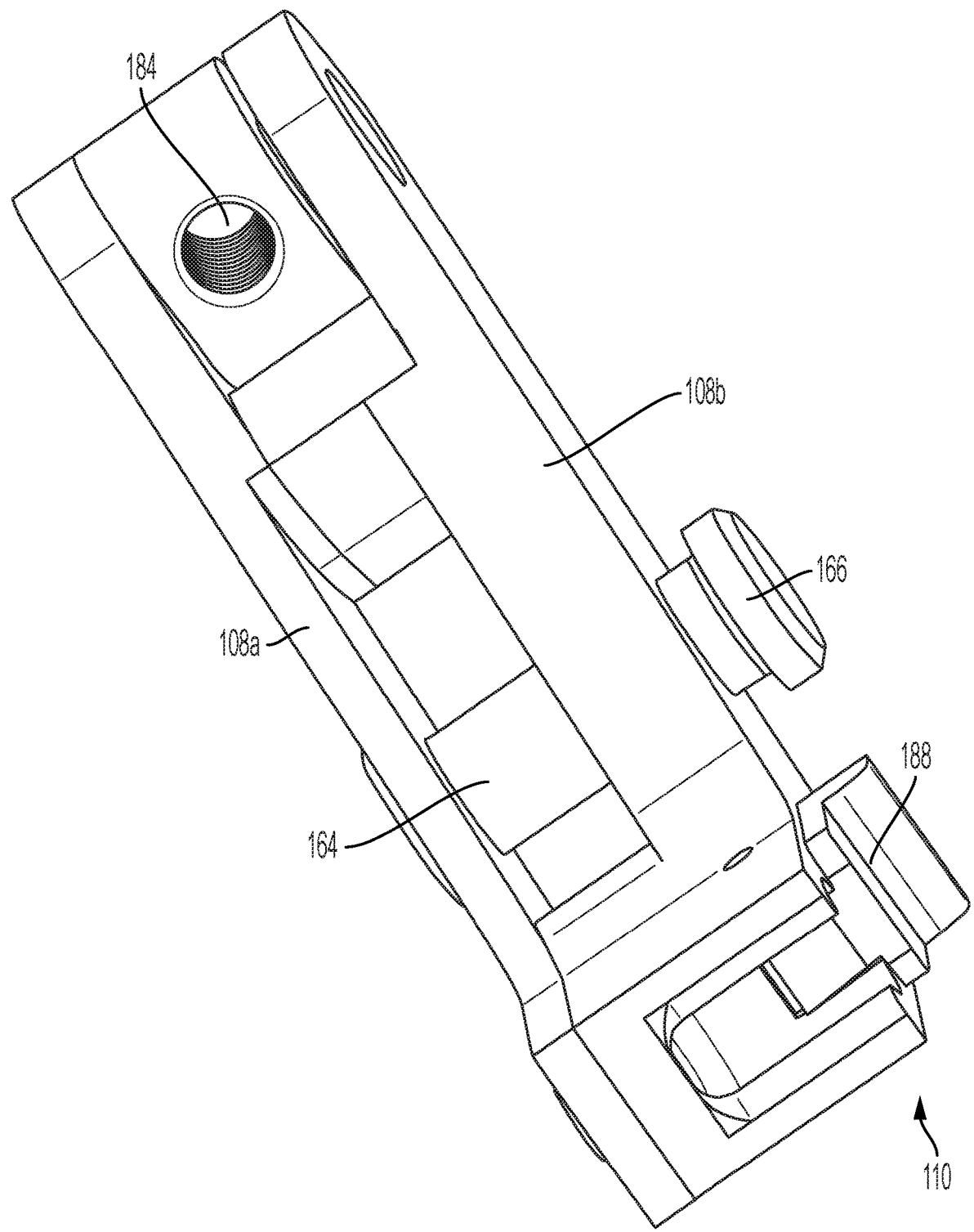
FIG. 11 is another bottom perspective view of the second arm of FIG. 10.
Figure 15:
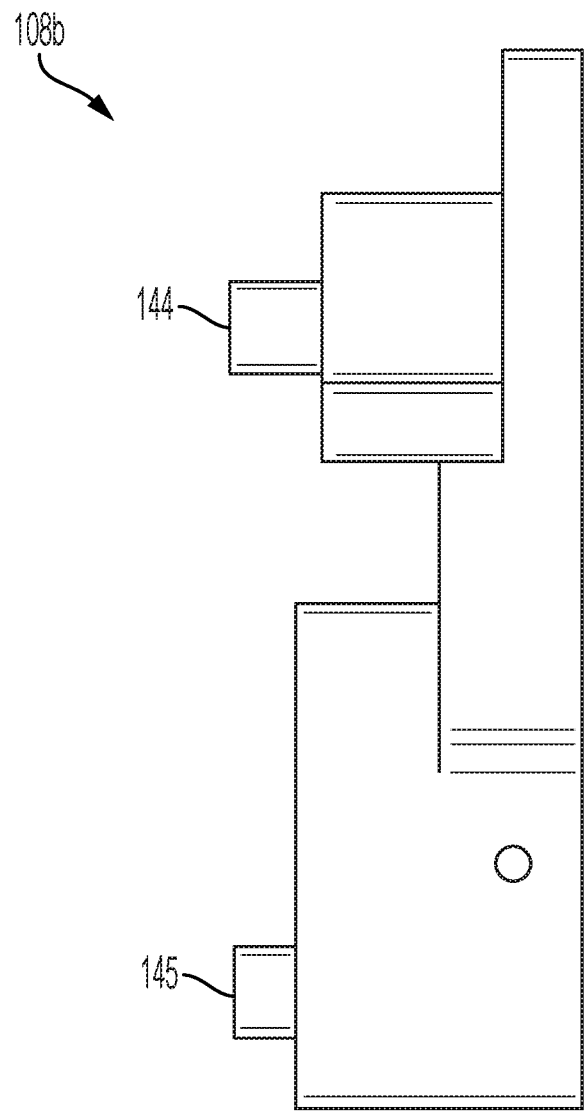
FIG. 15 is a side view of a left arm of the second arm of FIG. 13.

The second arm 108 includes a through hole 143 shaped to receive the pivot shaft 164. Projecting pins 144, 145 are provided as shown in FIGS. 10, 14 and 15 to secure the left arm 108b thereto. The second arm 108 is pivotably connected to the first arm 107 via the pivot 164 (that defines joint 120).

The second arm 108 includes the proximal end 136 which carries a cross-member 182. The cross-member 182 has a similar structure as cross-member 176 and includes oppositely faced pins 150, 153. Pin 150 is received by a through hole 155 in the right arm 108a and pin 153 is received by through hole 142 of the left arm 108b. The cross-member 182 further includes a bore 184, e.g., an internally threaded bore configured to threadedly engage with a threaded portion 186 of a shaft of the force applicator 126, as described below.

The distal end 110 of the second arm 108 includes a second latch 124 for releasably securing the second jaw 113 thereto. The second latch 124 includes a second socket 122 for releasably receiving the proximal end 177 of the second jaw 113.

Figure 12:
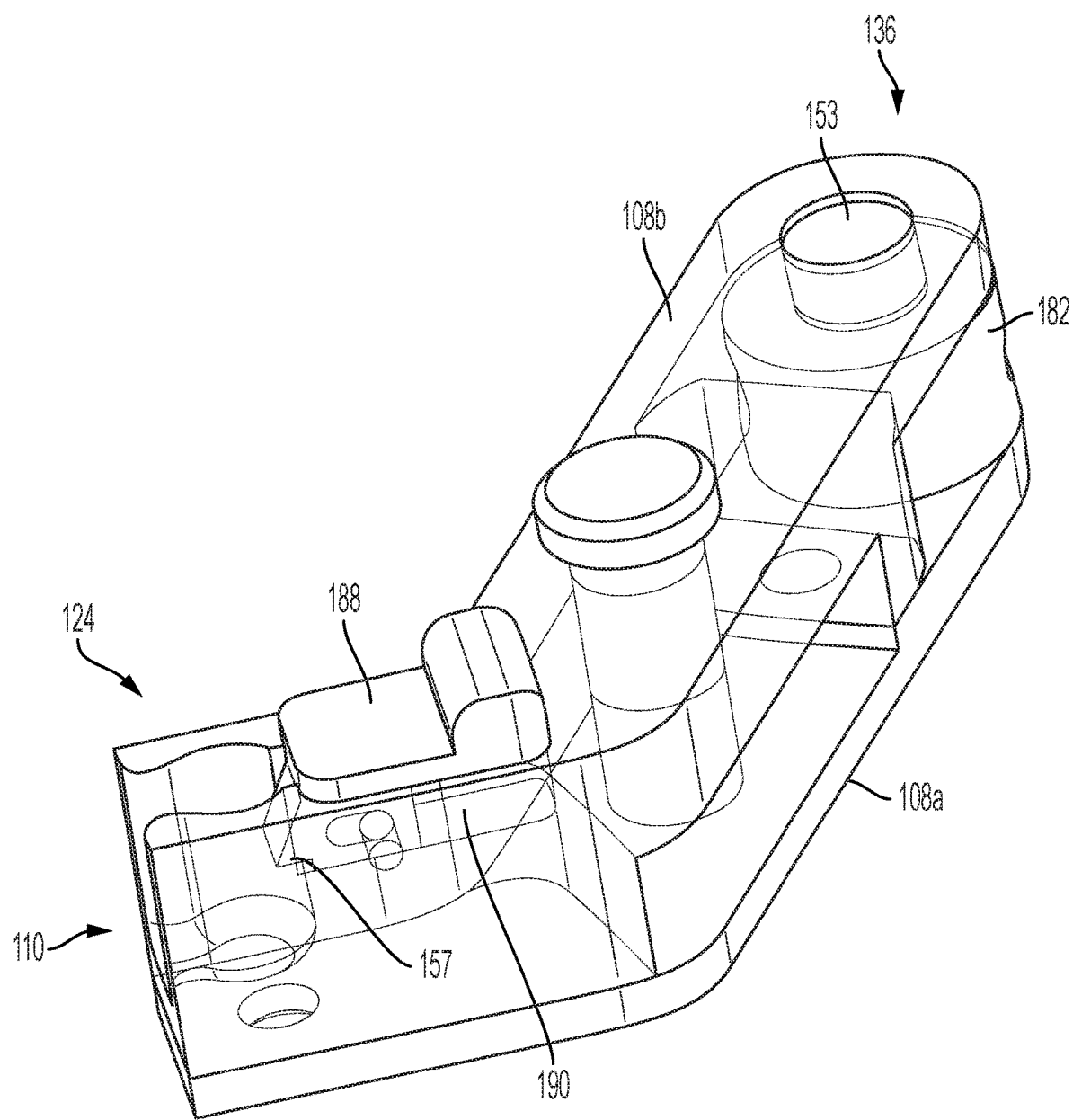
FIG. 12 is a perspective view of the second arm of FIG. 1, with certain portions shown in phantom for purposes of illustration.
Figure 13:
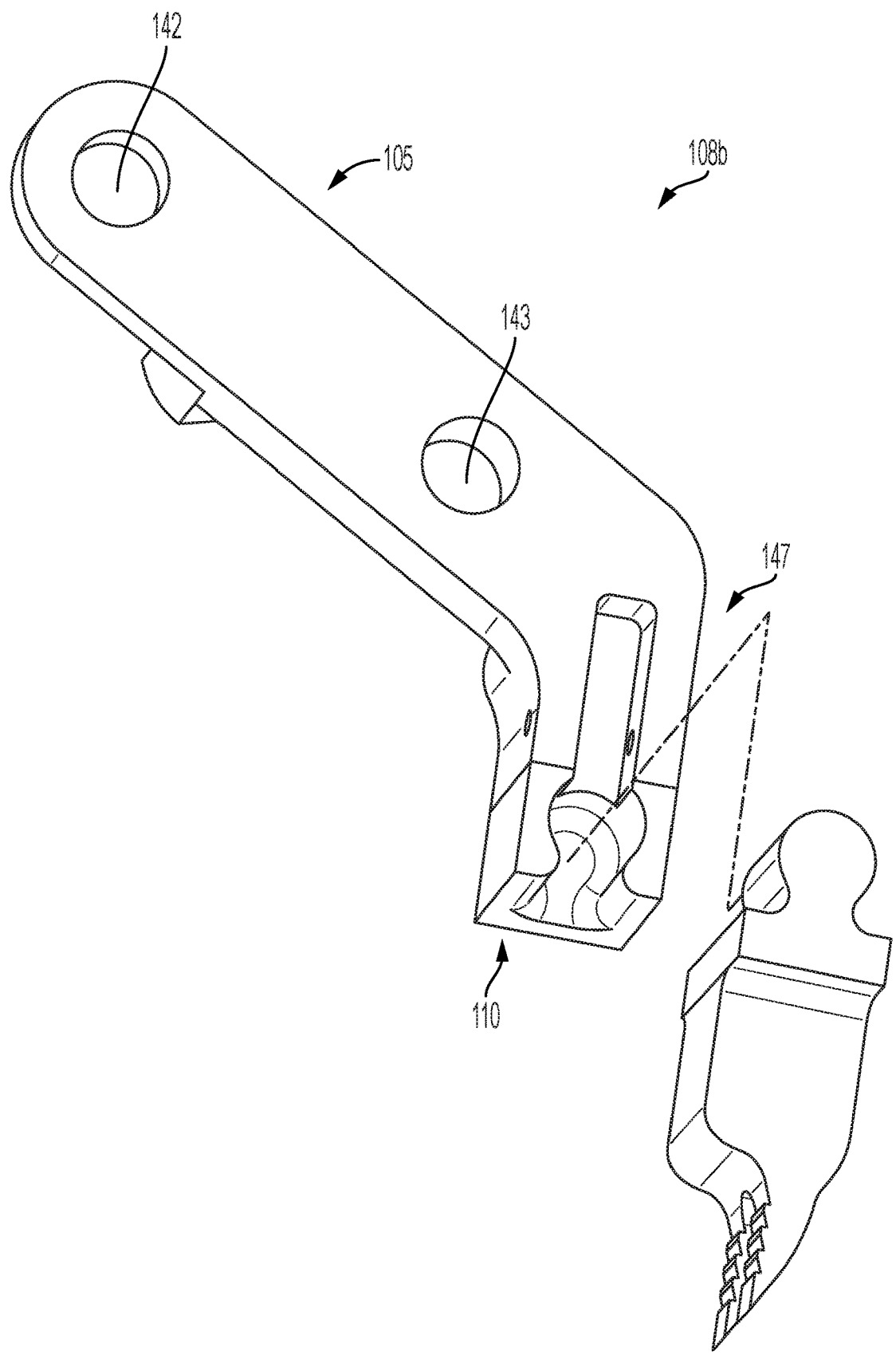
FIG. 13 is an isolated perspective view of a portion of the second arm of FIG. 1 and a jaw.

FIG. 12 shows an enlarged view of the second latch 124 for releasably securing the second jaw 113 to the second socket 122. The second latch 124 is similar to the first latch 118, described above. The second latch 124 includes a slidable actuator 188 moveable between first and second latching and unlatching positions to lock and unlock the second jaw 113. The slidable actuator 188 is operatively connected with a biased latch member 190 to allow the latch member 190 to be moved against the bias of a compression spring (not shown) or other biasing member. More particularly, in this particular embodiment, the slidable actuator 188 has a back side to which a biased latch member 190 is fixedly connected. The latch member 190, via a projecting notch 157, releasably engages with a notch 179 provided on a proximal end 177 of the second jaw 113 to releasably secure the second jaw 113 to the second socket 122.

Referring back to FIGS. 1 and 2, the force applicator 126 is operatively connected to the first arm and the moment arm to apply a force to one of the first and second arms. For example, the force applicator can provide an upward force F on the proximal end 136 of the second arm 108. Although the force applicator is described below in connection with a screw displacement device, other force applicators can be provided to apply a force to one or both of the first and second arms in accordance with presently disclosed subject matter.

Figure 16:
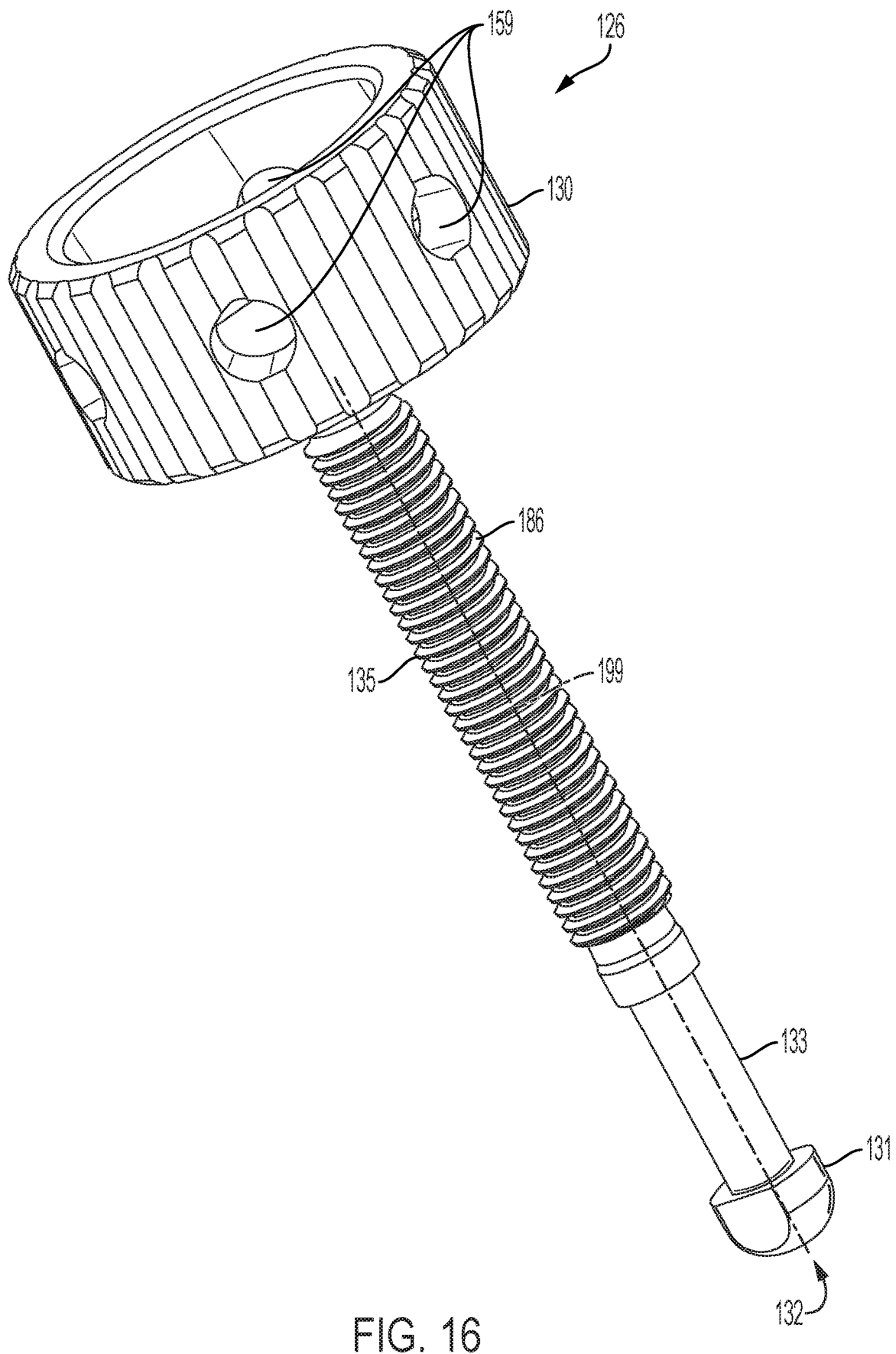
FIG. 16 is a perspective view of a force applicator of the implant extractor of FIG. 1.

An exemplary force applicator 126 is shown in FIG. 16. The force applicator 126 includes a thumb screw 130 operatively connected with a shaft 135. The outer periphery of the thumb screw 130 contains one or more orifices 159 shaped to receive a shaft of a tool (e.g., a shaft of a screwdriver) to provide torque on the thumbscrew 130. The shaft 135 of the force applicator 126 includes a proximal threaded portion 186 and a recessed, non-threaded portion 133 having a circular longitudinal cross-sectional shape. The shaft 135 has a longitudinal axis 199 which in this exemplary embodiment is parallel to the longitudinal axis 117 of the elongated body.

The force applicator 126 has a distal end 132 about which a knob 131 is provided to retain the cross-member 176. The recessed, non-threaded portion 133 of the shaft 135 is provided between the knob 131 and the threaded portion 186 of the shaft. This recessed, non-threaded portion 133 of the shaft 135 is rotatably received by orifice 137 in the cross-member 176 (FIGS. 7 and 8). The cross-member 176 is attached to the tail end 128 of the first arm 107. The threaded portion 186 of the shaft 135 threadedly engages with the threaded bore 184 of the cross-member 182 of the second arm 108 for axial translation of the proximal end 136 of the second arm 108 about the threaded portion 186 of the shaft 135 upon rotation of the thumb screw 130. As shown as assembled in FIG. 2, the proximal end 136 of the second arm 108 can be positioned directly above the tail end 128 of the first arm, each centered about the shaft 135 and longitudinal axis 132 of the force applicator 126.

In operation, rotation of the thumb screw 130 in the clockwise direction 134 of the double headed arrow in FIG. 1 causes the cross-member 182 at the proximal end 136 of the second arm 108 to raise along the threaded portion 186 of the shaft 135 of the force applicator 126 and the distal end 110 of the second arm 108 to pivot toward the distal end 106 of the first arm 107. In so doing, the second jaw 113 carried by the distal end 110 of the second arm 108 moves toward the first jaw 112 carried by the distal end 106 of the first arm 107 until the first jaw 112 and the second jaw 113 come into clamping engagement with an unillustrated implant to be extracted (e.g., clamping engagement with a shoulder implant implanted into the humerus for purposes of shoulder revision surgery). Once the first and second jaws are firmly engaged with the implant, an extraction force can be applied by the extraction device to extract the implant from the bone in which it resides.

When the force applicator 126 provides a upward force, F, on the proximal end 136 of the second arm 108, the force is directed at the moment arm 105, which is that part of the second arm from the proximal end 136 to joint 120. Joint 120 is formed through through hole 143 of the left arm.

The implant extractor of the subject disclosure provides a lever advantage due to its configuration. More particularly, as shown for example in FIGS. 1 and 2, the moment arm 105, from the proximal end 136 to the joint 120 is significantly longer than any other arm segment from the joint 120. For example, with reference to FIG. 2, the length of the functional moment arm "M" can be at least 1.25, 1.5, 1.75, or 2.0 times longer than the length "A" of the second arm. Length "M" is measured from the line action of force provided by the force applicator 126 to joint 120, length "A" is measured from joint 120 to the center longitudinal axis 148 of the distal arm segment 147.

Stated differently, as can be readily seen, for example, in FIGS. 1, 2 and 14, the moment arm 105 is longer than, (a) a distance of the first arm from the distal end 175 of the elongated body to the joint 120, (b) a distance of the first arm from the joint 120 to the distal end 106 of the first arm, and (c) the distance of the second arm from the joint 120 to the distal end 110 of the second arm. The longer moment arm 105 relative to all other moment arm lengths to the first and second arms will provide relatively higher torques on the second jaw 113 which in turn will provide a higher clamping force to the implant to be extracted.

Figure 17:
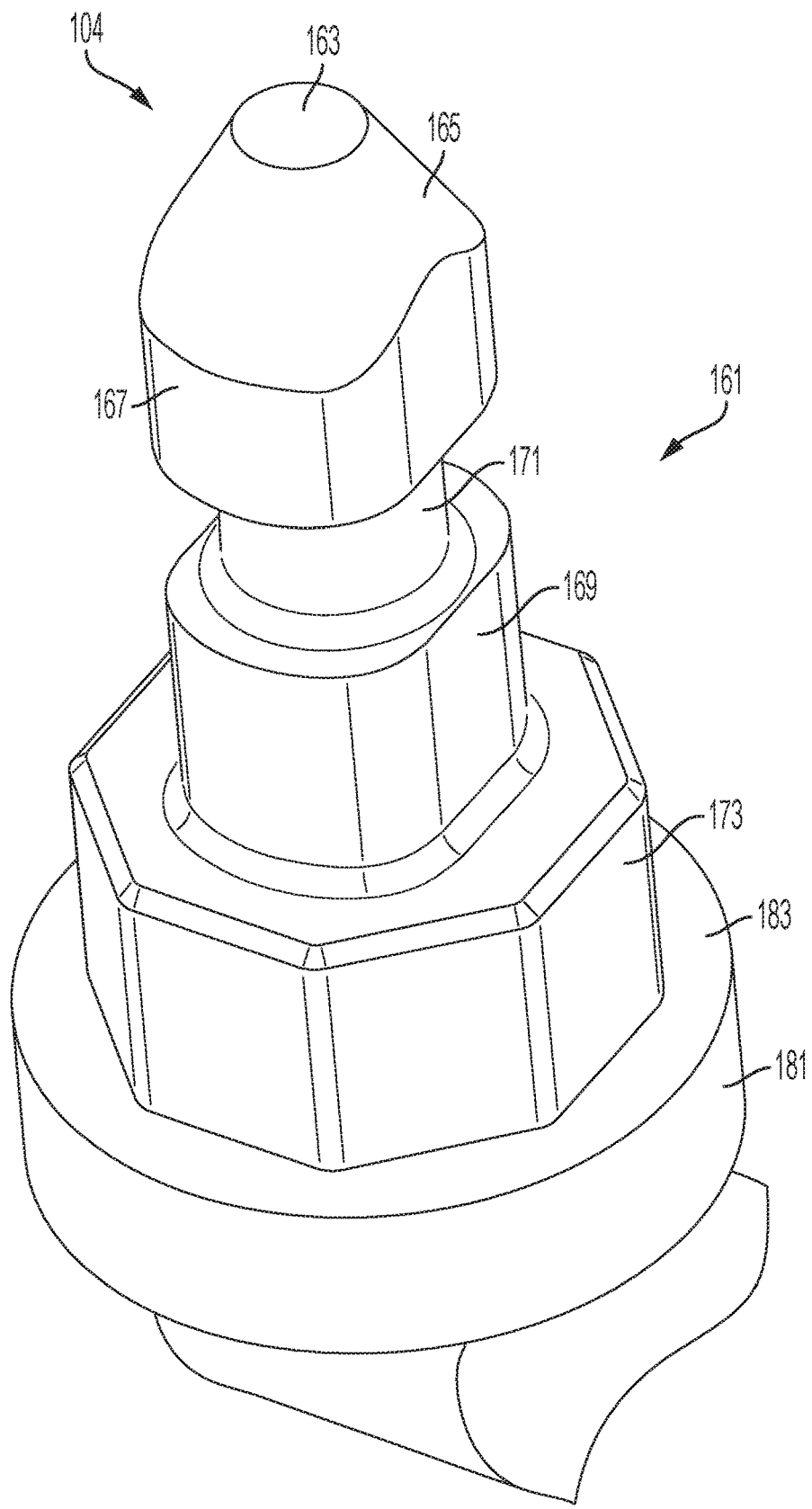
FIG. 17 is a partial perspective view of a proximal end of the elongated body of FIG. 1.
Figure 18:
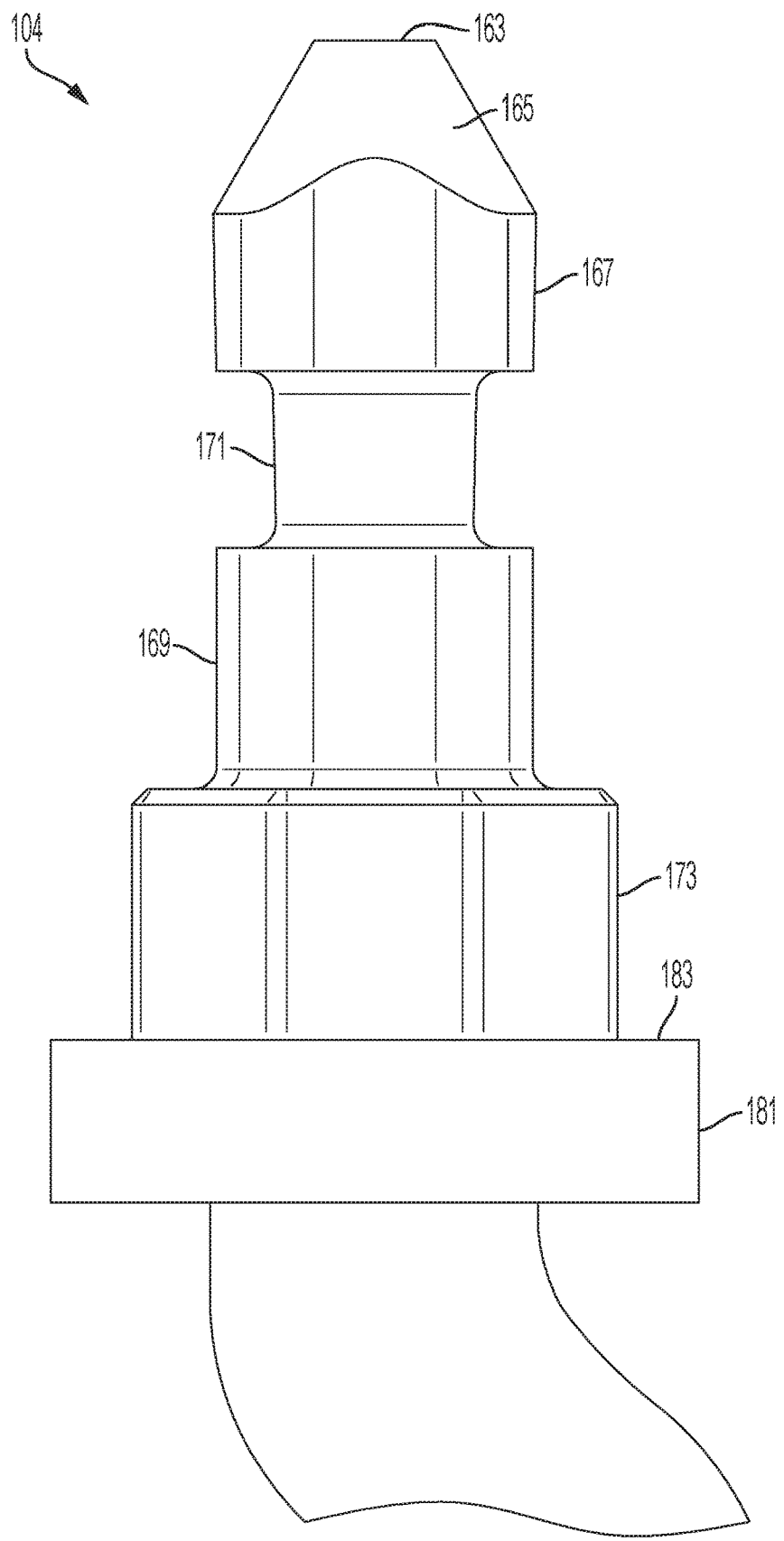
FIG. 18 is an elevational view of FIG. 17.
Figure 19:
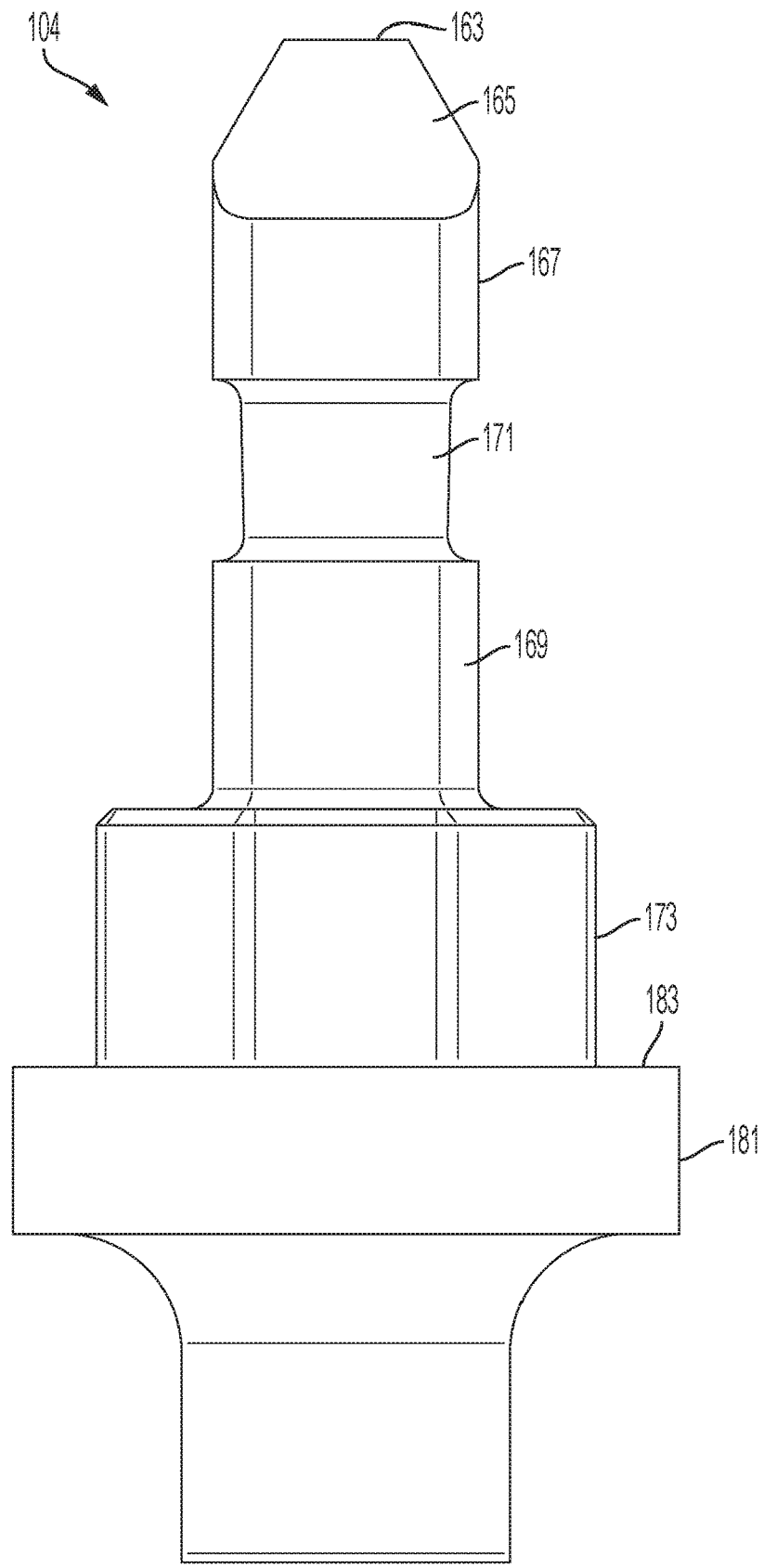
FIG. 19 is another elevational view of FIG. 17.

FIGS. 17-19 depict the proximal end 104 of the elongated body, which includes a quick connect 161. In this illustrative embodiment, the quick connect 161 includes a relatively small circular cross-section about the top 163 of the quick connect. A flare 165 extends distally from the top 163 to a first post 167 of the quick connect. The first post 167 has an oval or racetrack cross-sectional shape similar in size and cross-sectional shape to a second post 169 that is co-axial to the first post 167. An annular recess 171 is provided between the first post 167 and the second post 169 having a significantly smaller diameter than first and second posts. In this particular embodiment, the annular recess 171 has an oval or racetrack cross-sectional shape, though other configurations could be provided.

The second post 169 of the quick connect 161 is mounted or extends from a polygonal shaped block 173, which in this particular embodiment is in the shape of a regular octagon. The polygonal shaped block 173 is mounted or extends from a circular base 181. The circular base 181 has a diameter that exceeds the width of the polygonal shaped block to provide a plateau 183 which can support an extraction device (e.g., a base plate or striking plate).

Figure 20:
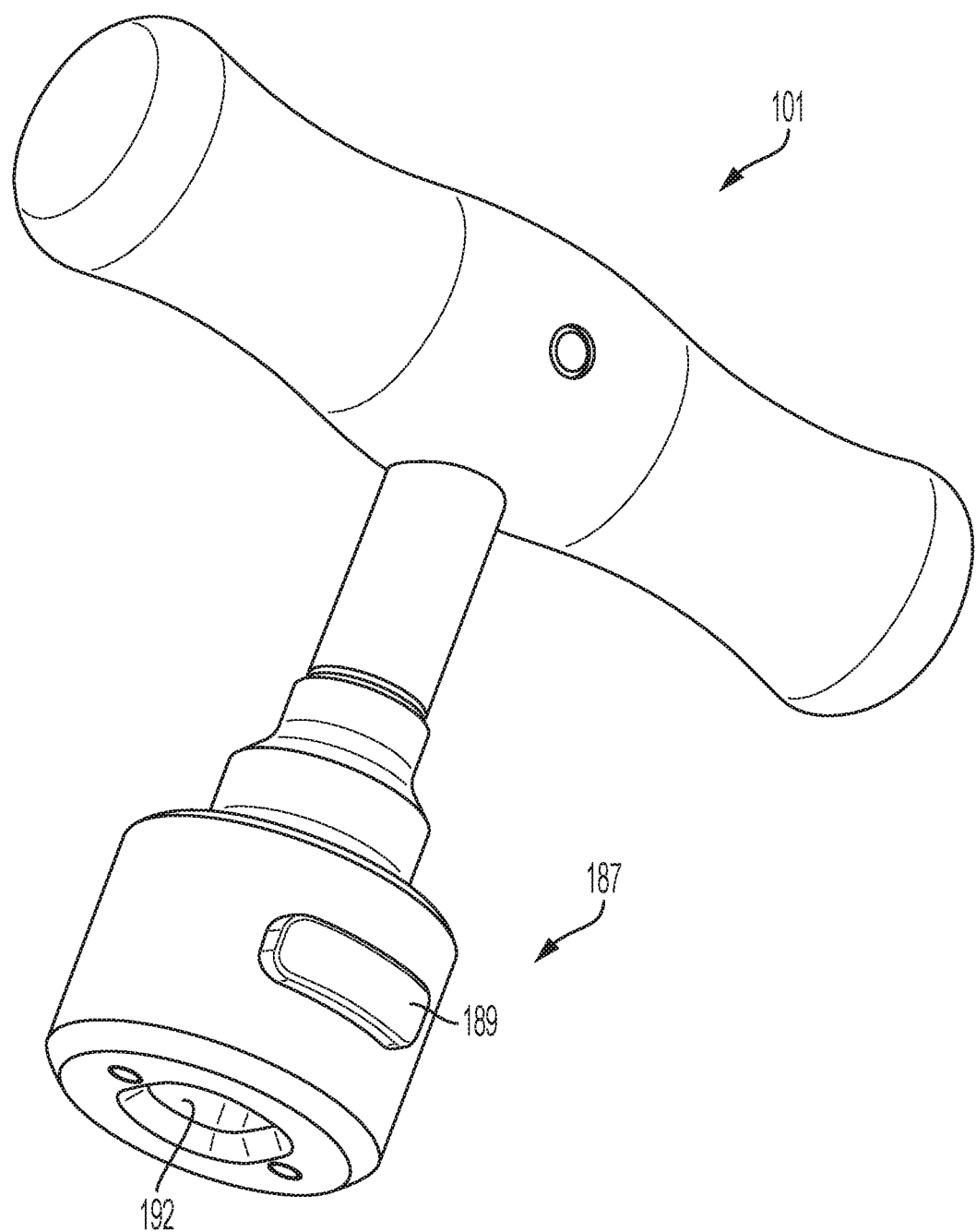
FIG. 20 is a perspective view of an exemplary extraction device applicable to the implant extractor of FIG. 1.
Figure 21:
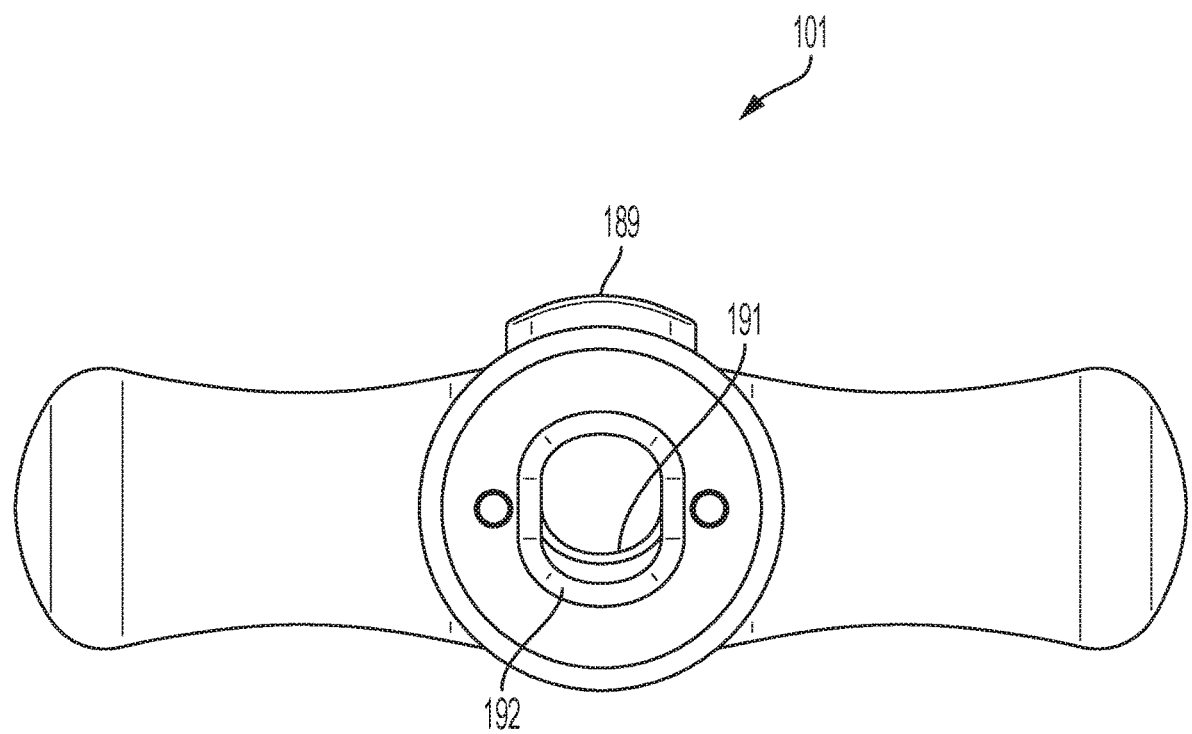
FIG. 21 is a bottom view of the extraction device of FIG. 20.

FIGS. 20-21 depict an exemplary extraction device 101, which is in the form of a T-handle. The extraction device connects with the attachment mechanism 103 about the proximal end 104 of the elongated body 102 via a cooperating quick connect 187 located about a distal end of the T-handle and including an orifice 192. The cooperating quick connect 187 includes an actuator 189 that is biased by a spring or other biasing mechanism (not shown). In the normally biased position shown in FIG. 21, an actuator aperture 191 is not aligned with a channel provided by the orifice 192 such that the channel provided by orifice 192 is partially obstructed by the spring-biased actuator 189. As the quick connect of the elongated body 102 is inserted into the cooperating quick connect 187 of the T-handle 101, the flare 113 will advance the actuator aperture 191 against the bias of a spring or other biasing member to force the actuator aperture in co-alignment with the channel provided by orifice 192 to accommodate the distally increasing diameter of the quick connect. Once the actuator reaches the annular recess 171 of the quick connect, the actuator 189 is allowed to return to its normally biased position, in which the channel provided by orifice 192 is again partially obstructed. The partially obstructed channel does not allow movement of the T-handle owing to the relatively larger diameters of the first post 167 and the second post 169 of the quick connect, and the T-handle is locked into place. To remove the T-handle, the actuator 189 is depressed to co-align the actuator aperture 191 with the channel provided by orifice 192 and allow the first post 167 to clear the actuator 189.

Figure 22:
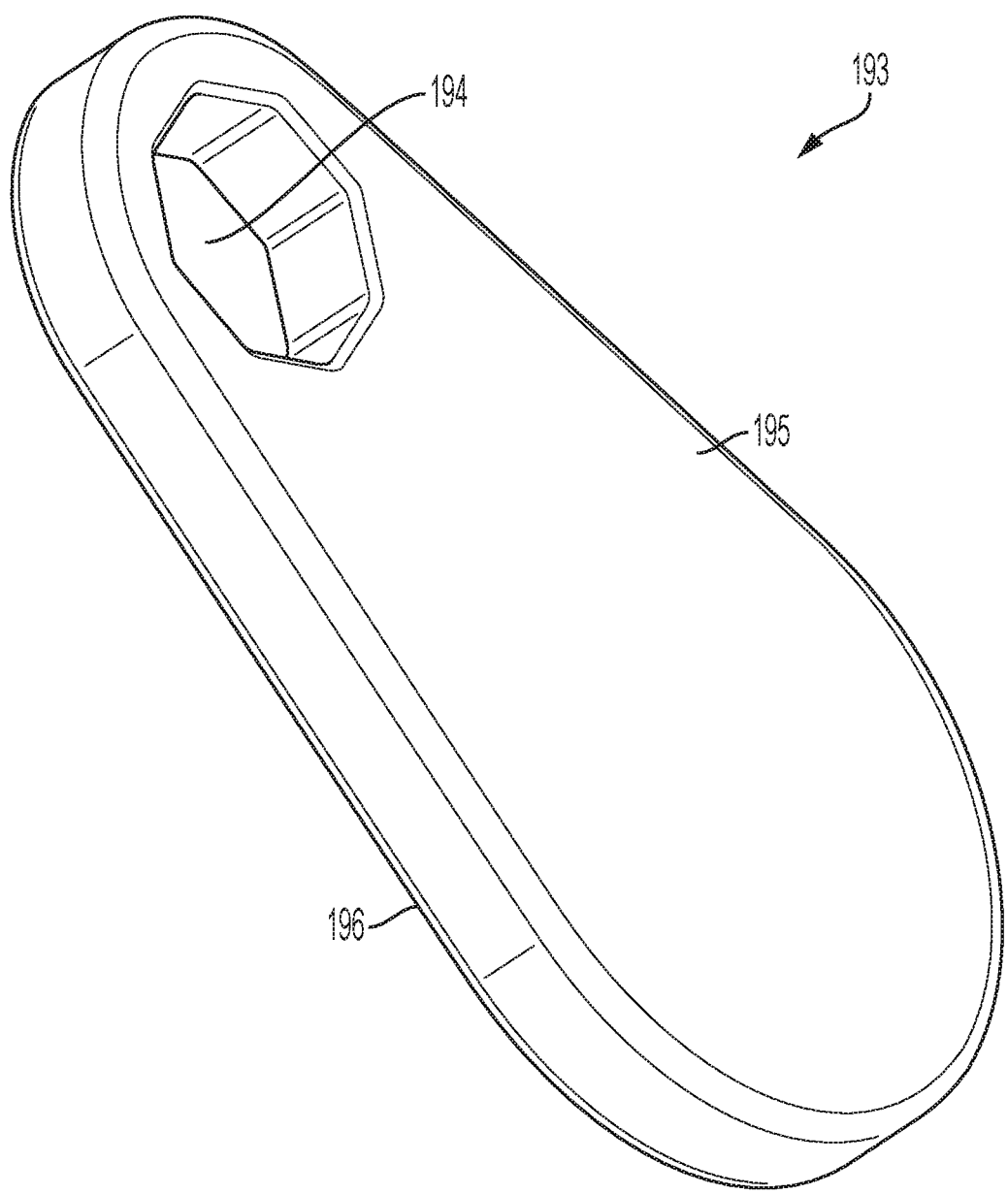
FIG. 22 is a perspective view of a striking member applicable to the implant extractor of FIG. 1.
Figure 23:
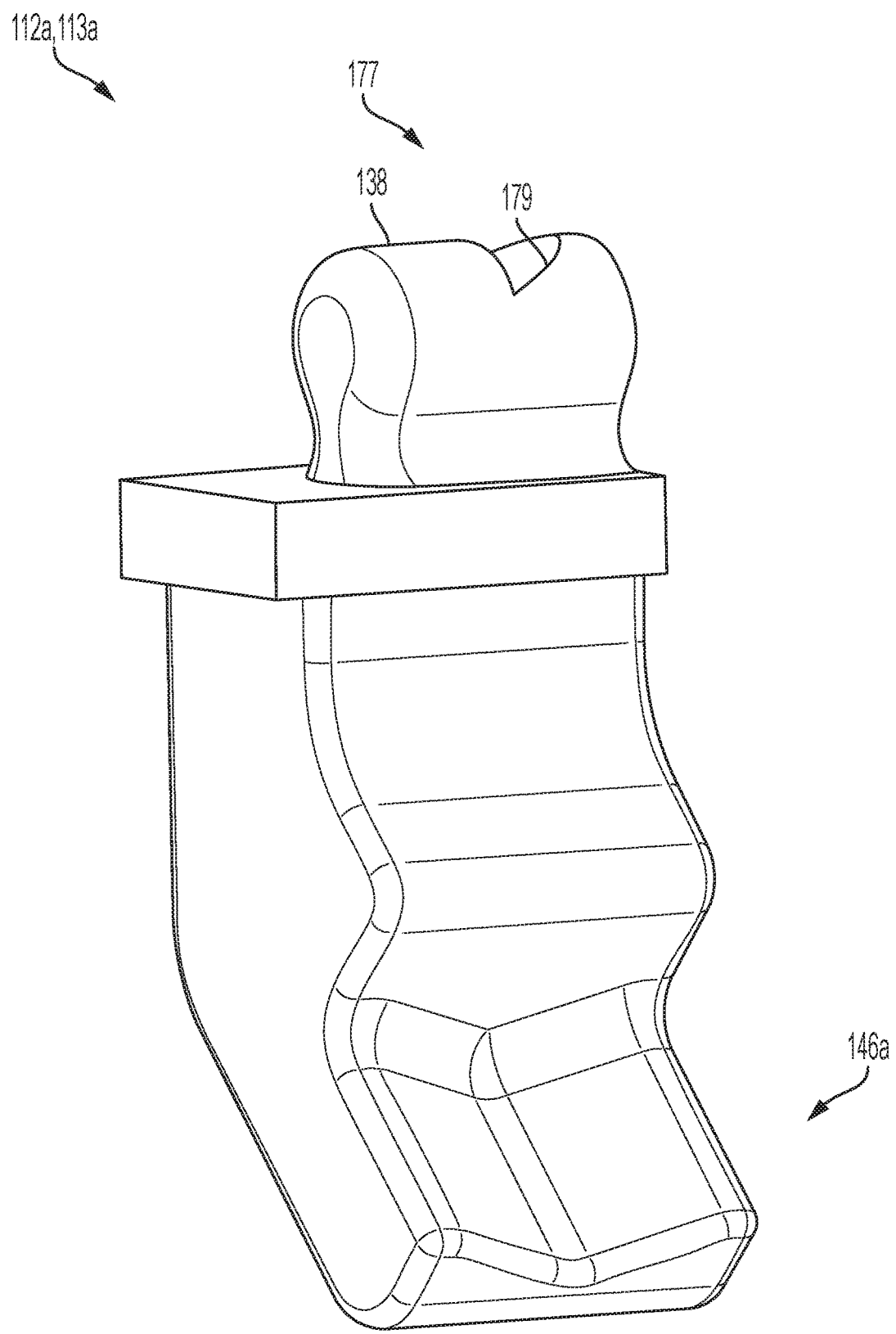
FIG. 23 is a perspective view of a first jaw and/or a second jaw according to an exemplary embodiment of the subject disclosure applicable to the implant extractor of FIG. 1.
Figure 24:
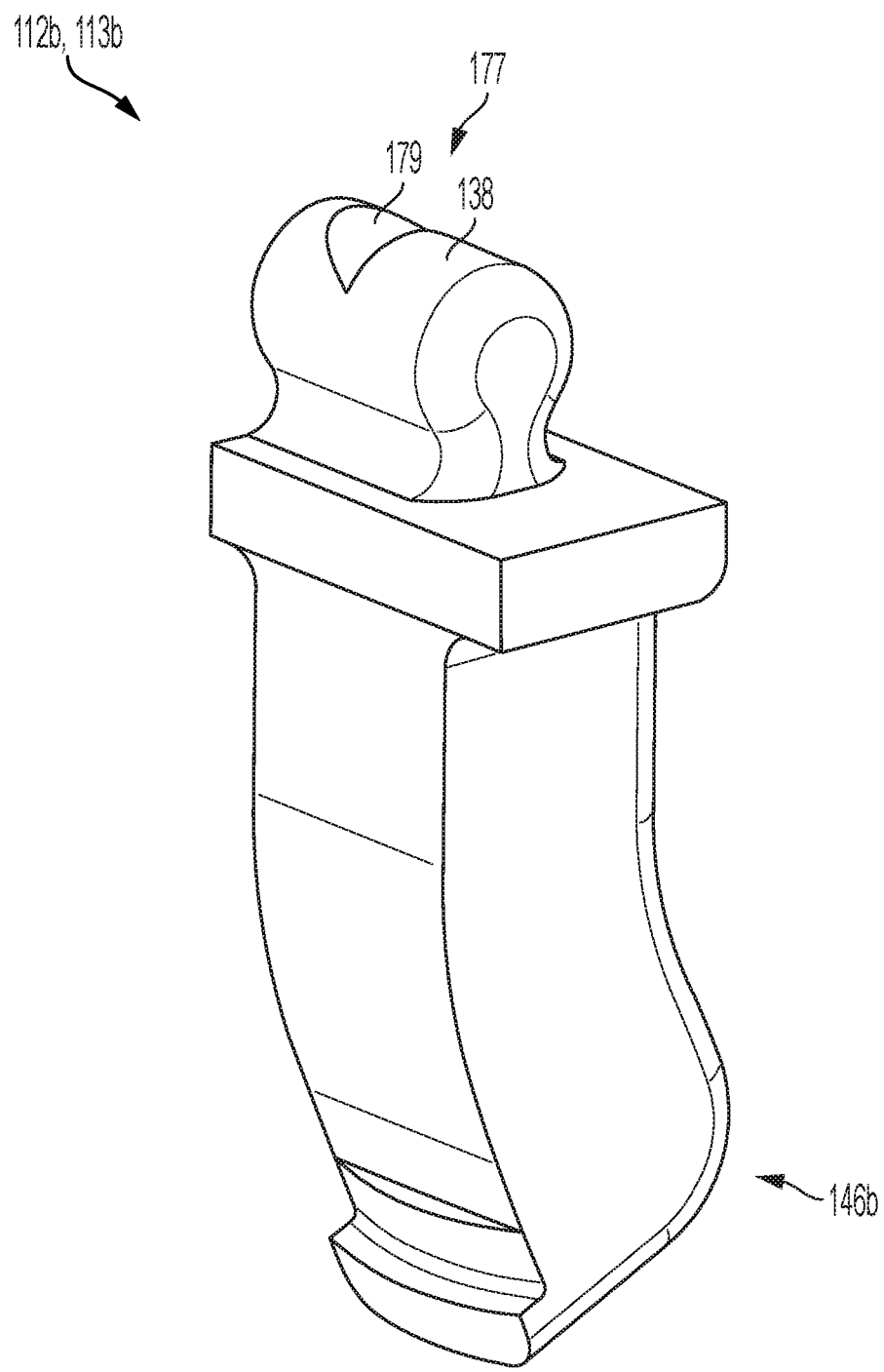
FIG. 24 is a perspective view of a first jaw and/or a second jaw according to another exemplary embodiment of the subject disclosure applicable to the implant extractor of FIG. 1.
Figure 25:
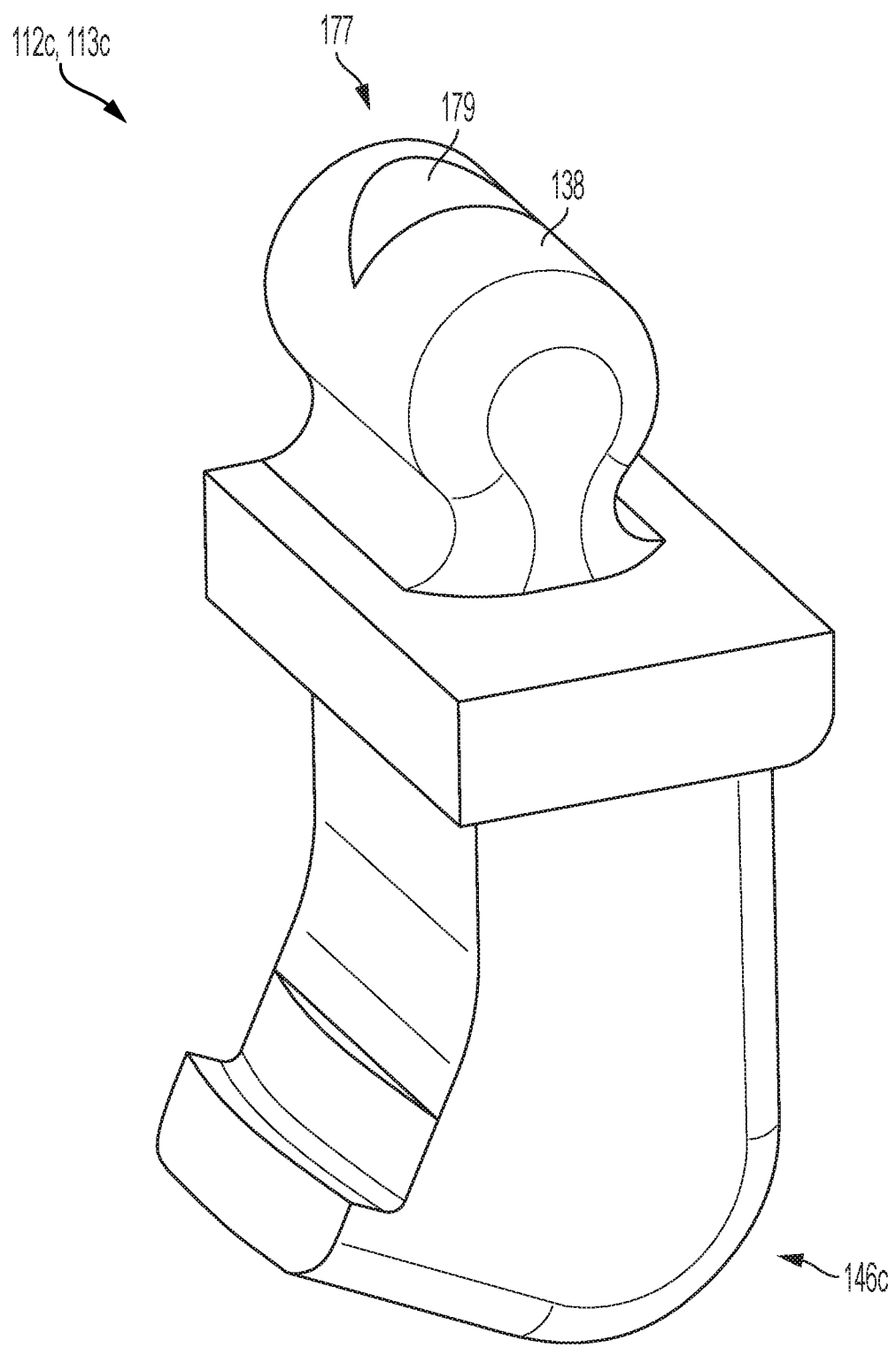
FIG. 25 is a perspective view of a first jaw and/or a second jaw according to another exemplary embodiment of the subject disclosure applicable to the implant extractor of FIG. 1.
Figure 26:
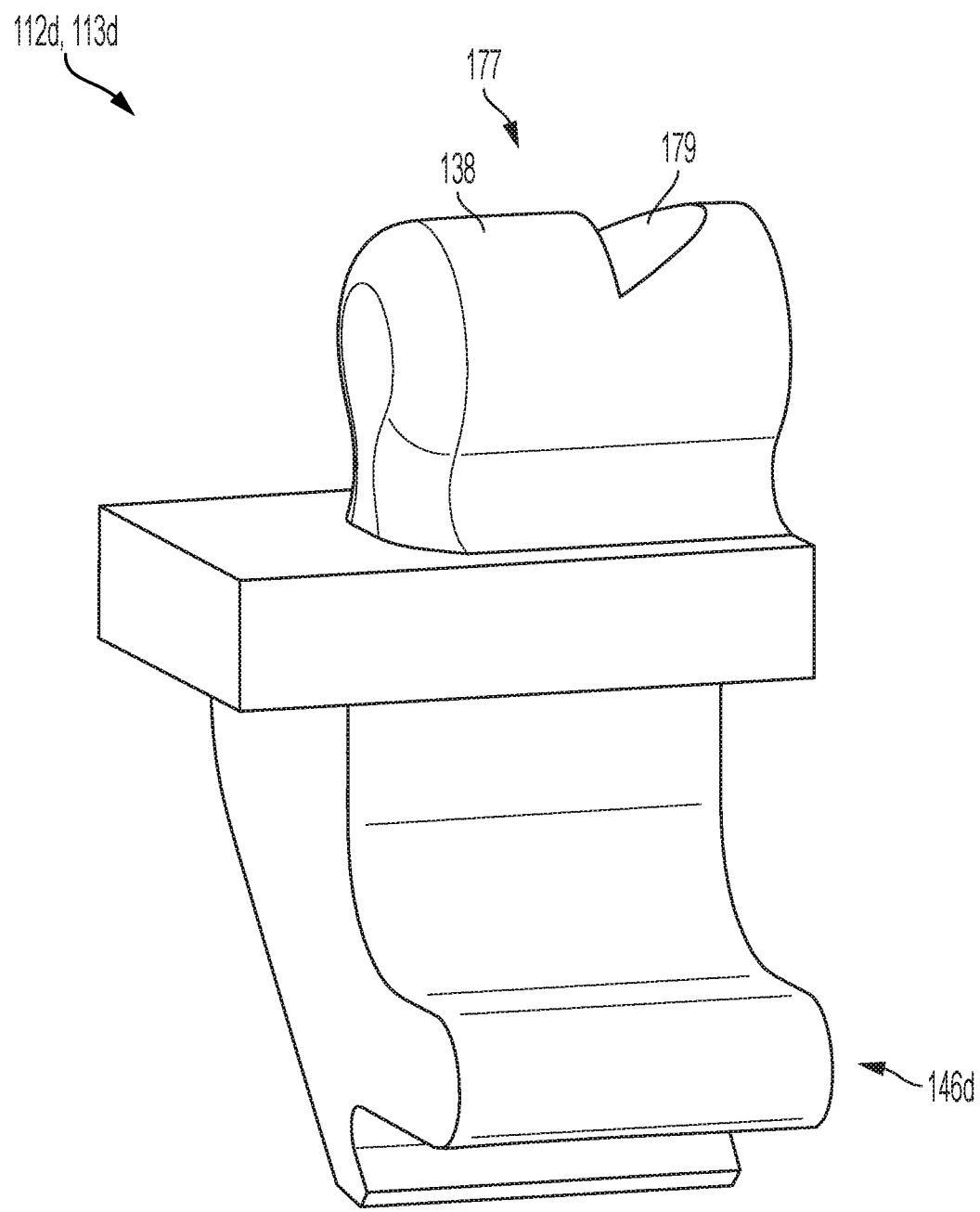
FIG. 26 is a perspective view of a first jaw and/or a second jaw according to another exemplary embodiment of the subject disclosure applicable to the implant extractor of FIG. 1.
Figure 27:
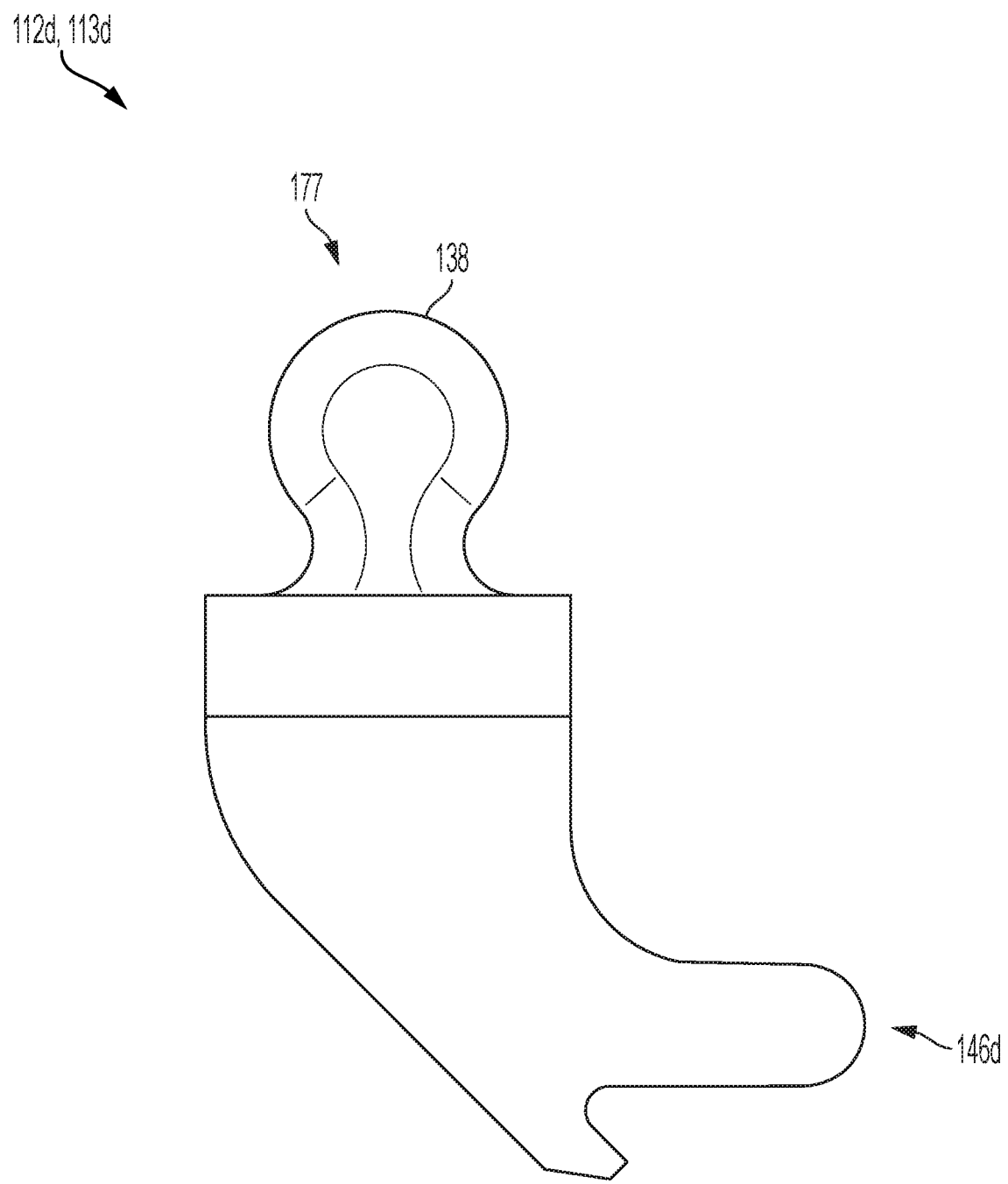
FIG. 27 is an elevational view of the jaw of FIG. 26.
Figure 28:
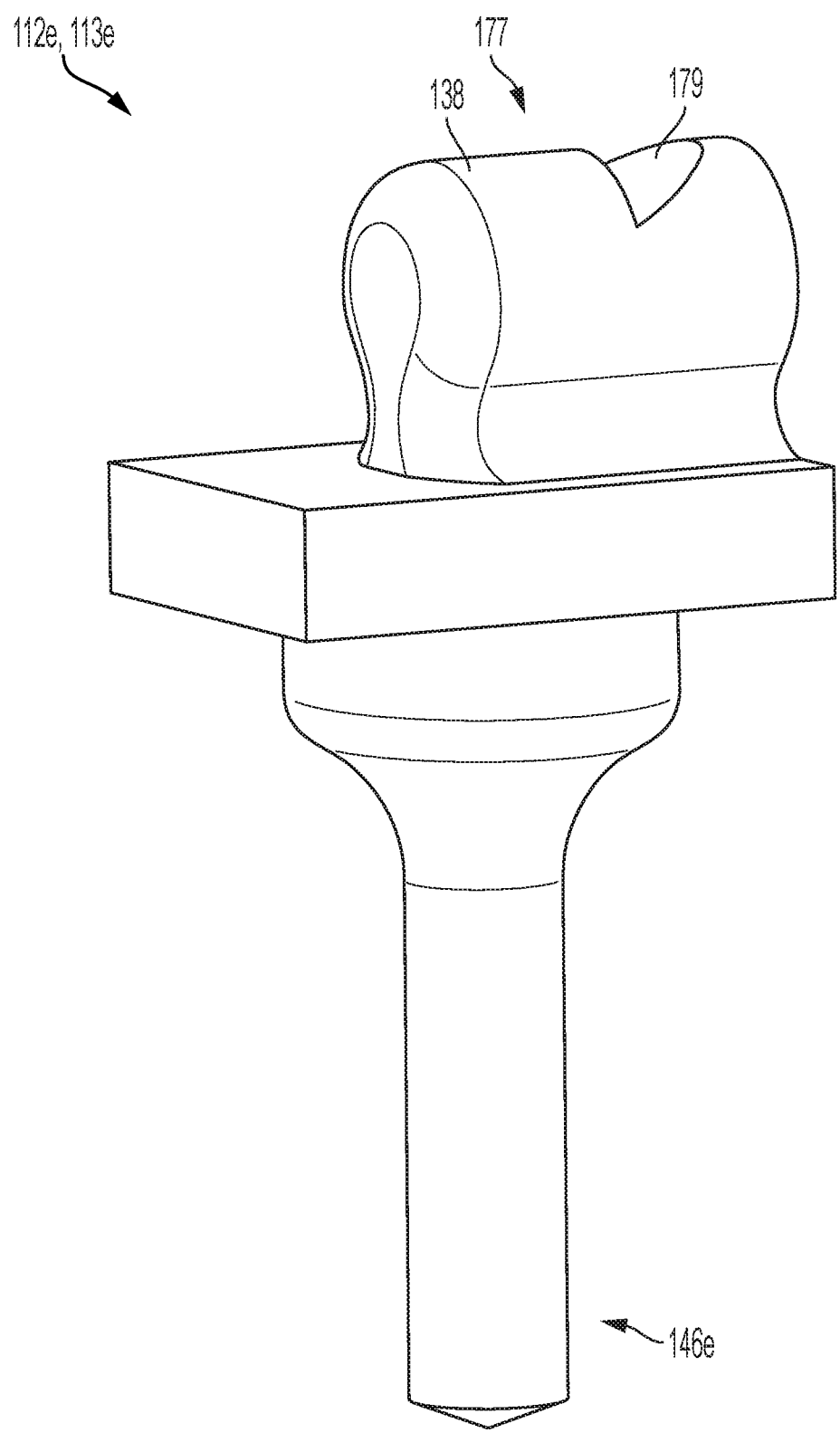
FIG. 28 is a perspective view of a first jaw and/or a second jaw according to another exemplary embodiment of the subject disclosure applicable to the implant extractor of FIG. 1.

FIG. 22 discloses another extraction device in the form of a striking member or striking plate 193. The striking member 193 includes an aperture 194 that has a shape that corresponds to the shape of the polygonal-shaped block 173, which in this exemplary embodiment is in the shape of a regular octagon. The striking member 193 has a pair of opposite planar faces 195, 196 having an increasing width about an end opposite the aperture 194 to provide a surface for striking the striking member 193 with e.g., a surgical hammer (not shown). The striking member 193 can be used alone, or in conjunction with a T-handle or other extraction device. In other exemplary embodiments of the implant extractor, a striking member is not used.

Referring to FIGS. 23-33, there are shown several exemplary, although non-limiting, configurations of jaws 112, 113 that may be releasably connected to the first and second sockets 116 and 122 of the first arm 107 and the second arm 108.

The proximal ends of jaws 112, 113 include male members 138 configured to be received in the first and second sockets 116 and 122 of the first arm 107 and the second arm 108. Notch 179, shaped complimentary to latch members 178, 190, is configured to receive the biased latch members 178, 190 of the slidable actuators of the first and second latches 118, 124 for the first and second jaws 112, 113.

Figure 32:
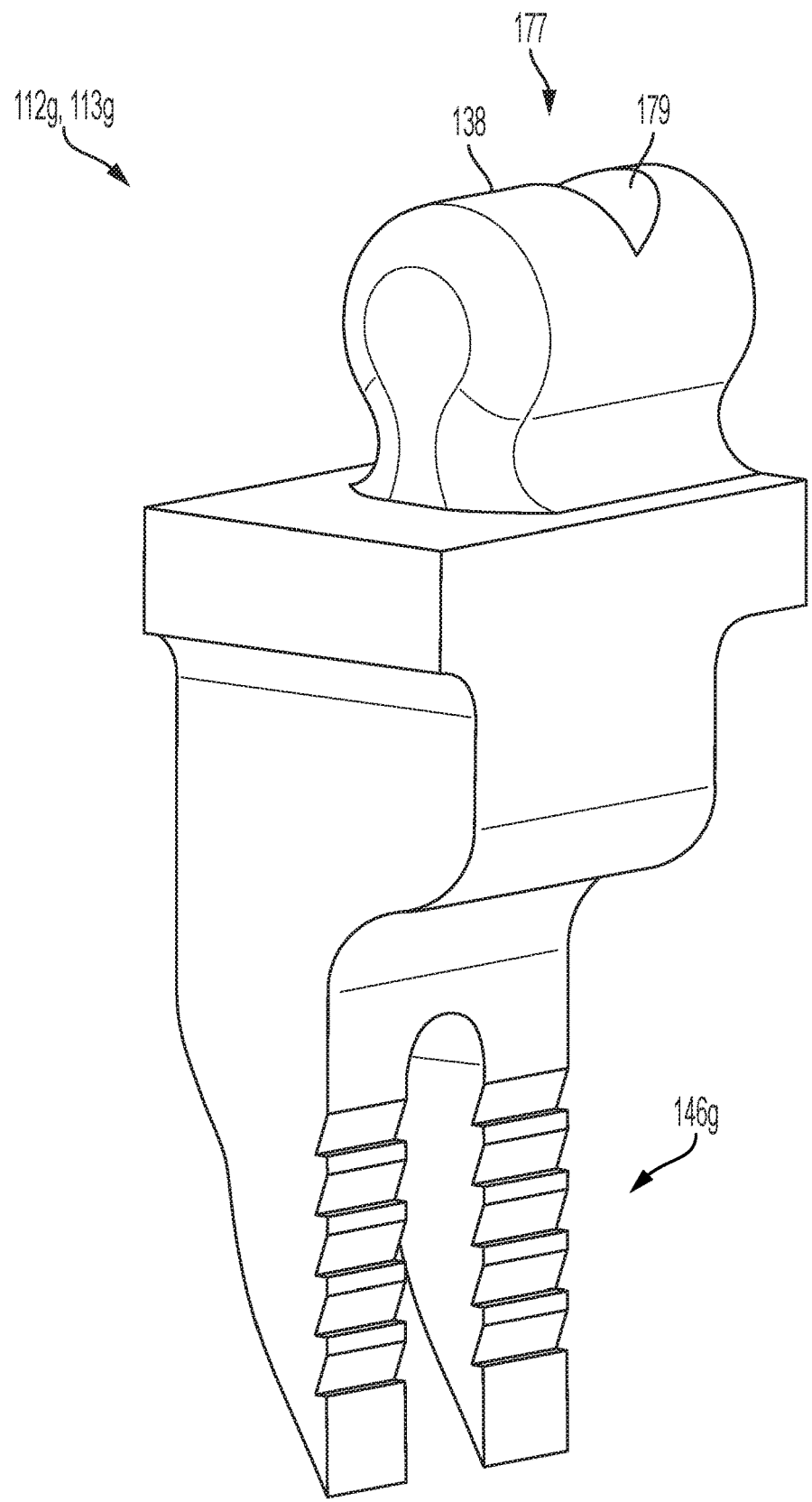
FIG. 32 is a perspective view of a first jaw and/or a second jaw according to another exemplary embodiment of the subject disclosure applicable to the implant extractor of FIG. 1.
Figure 33:
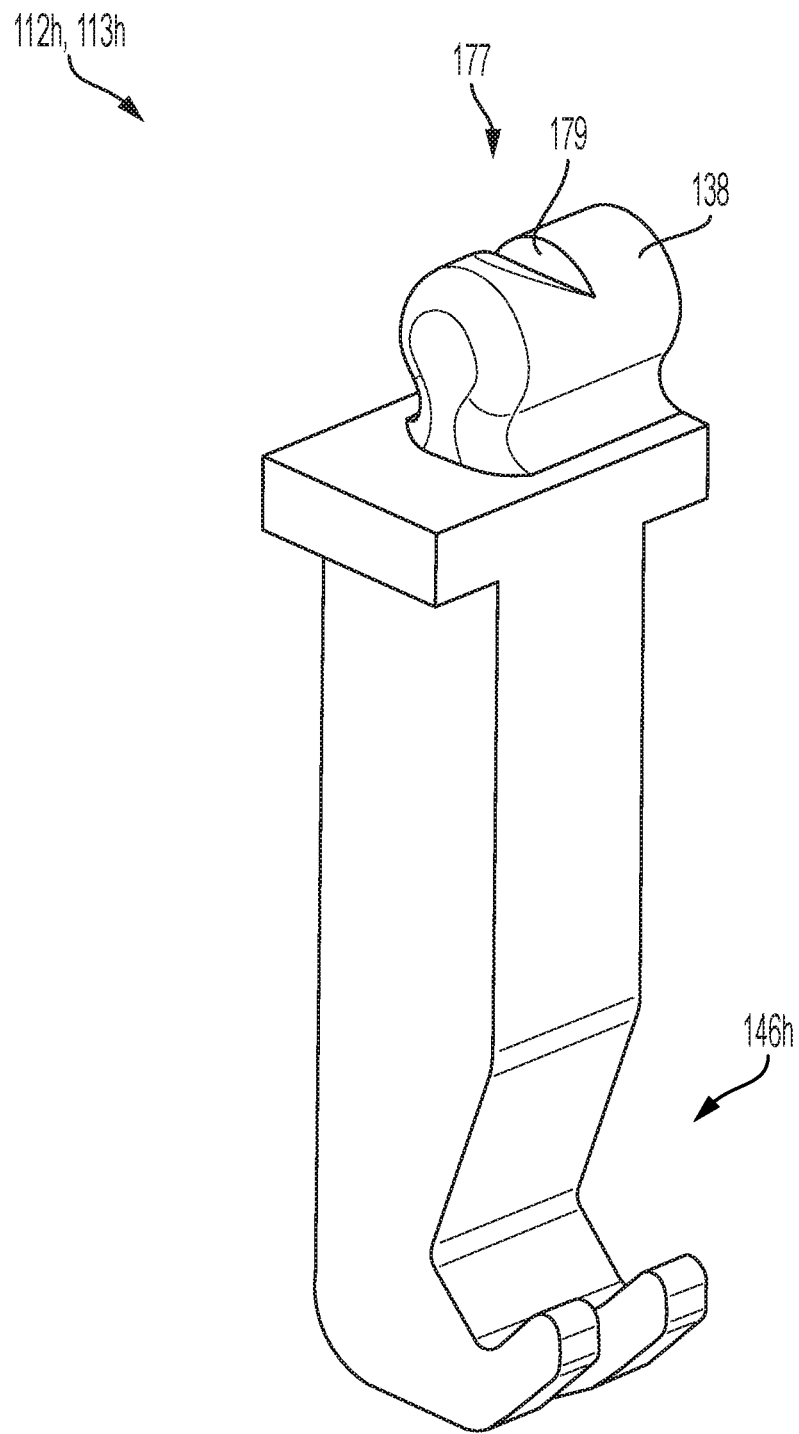
FIG. 33 is a perspective view of a first jaw and/or a second jaw according to another exemplary embodiment of the subject disclosure applicable to the implant extractor of FIG. 1.

The distal ends or portions 146a-h of jaws 112a-h, 113a-h are configured to be substantially cup-shaped 146a (FIG. 23), substantially curved 146b (FIG. 24), J-shaped 146c (FIG. 25), substantially boot-shaped 146d (FIGS. 26-27), substantially cylinder or substantially vertical cylinder shaped 146e (FIG. 28), substantially dog-leg shaped 146f (FIGS. 29-31), substantially toothed-prong shaped 146g (FIG. 32), or hooked-prong shaped 146g (FIG. 33).

Figure 29:
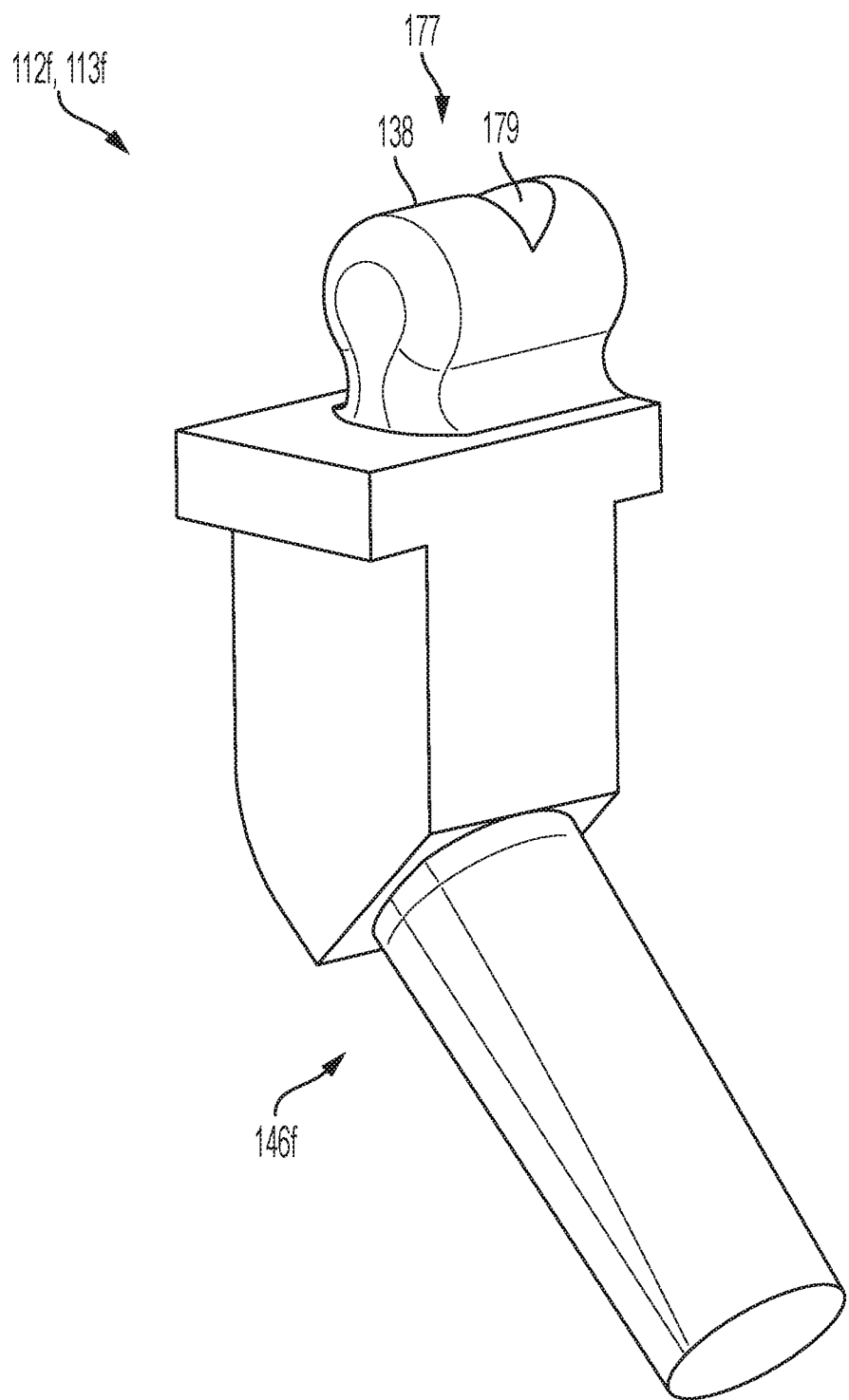
FIG. 29 is a perspective view of a first jaw and/or a second jaw according to another exemplary embodiment of the subject disclosure applicable to the implant extractor of FIG. 1.
Figure 30:
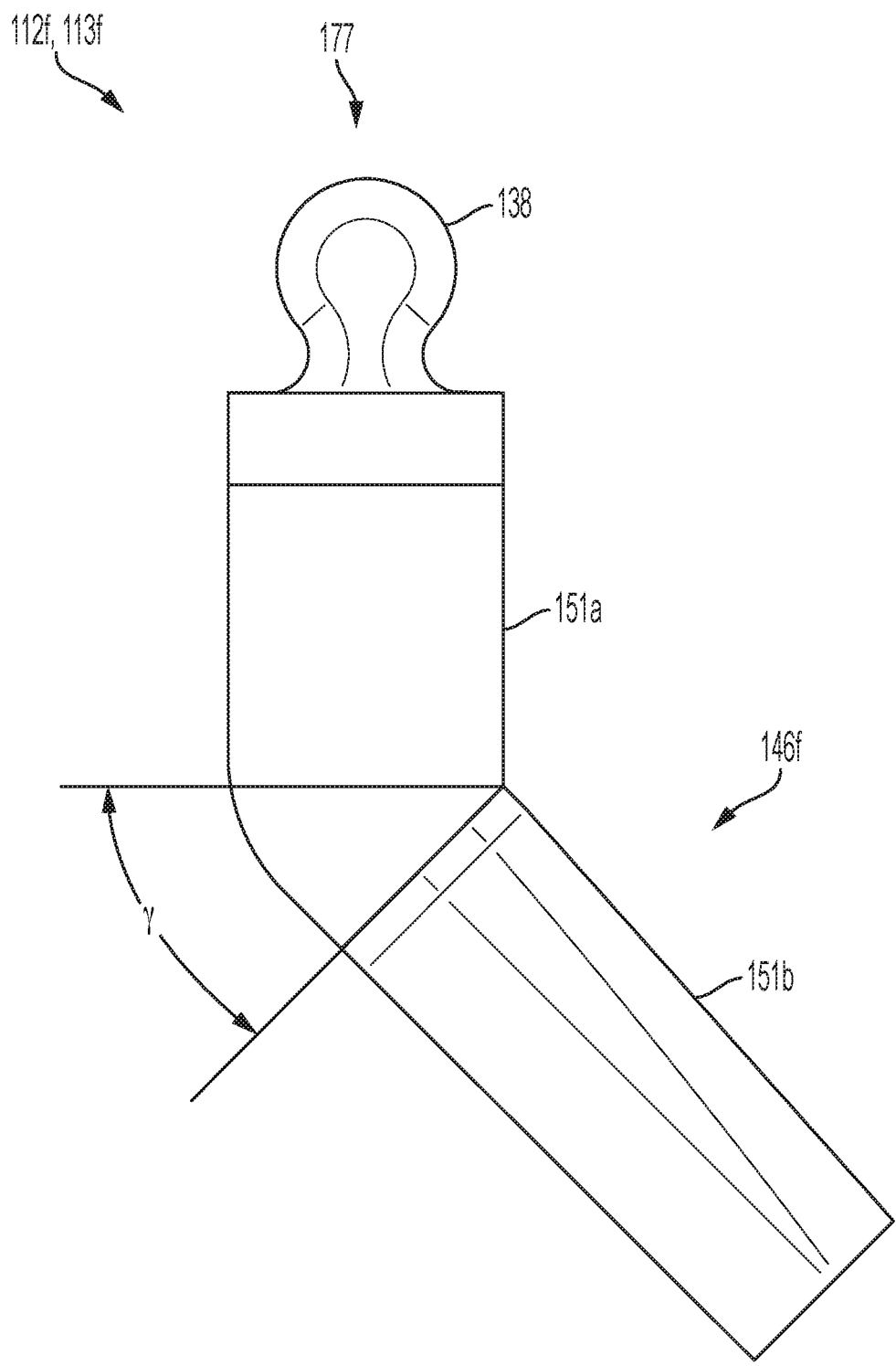
FIG. 30 is an elevational view of the jaw of FIG. 29.
Figure 31:
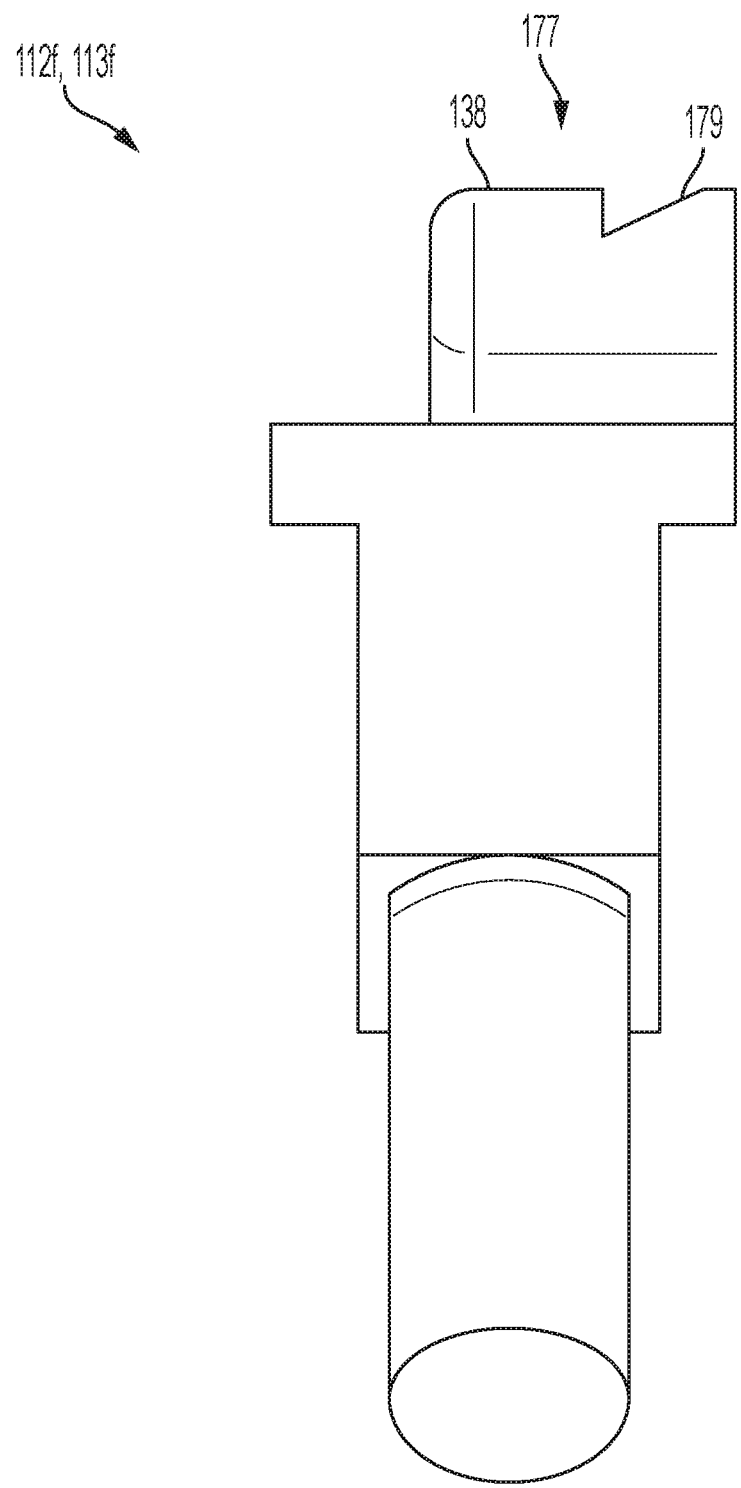
FIG. 31 is a perspective view of the jaw of FIG. 29.

As for FIGS. 29-31, the dog-leg shape is provided by a block-like upper portion 151a connected at its lower end at an acute angle, γ, of between about 30-60 degrees to a lower gripping portion 151b. As illustrated in FIGS. 29-31, the lower gripping portion 151b can be substantially cylindrical to substantially frustoconical in shape. It is understood that the user selects the appropriately shaped jaws for securement in the first and second sockets 116 and 122 of the first arm 107 and the second arm 108 based on the configuration of the implant to be extracted. Other configurations can be provided in accordance with the subject disclosure.

In general, the jaws disclosed in FIGS. 23-33 are interchangeable, e.g., any one of the disclosed jaw embodiments can be used as the first jaw 112 or the second jaw 113. In one particular embodiment, the jaw embodiment 112g, 113g shown in FIG. 32 is employed as the second jaw 113 that is connected to the distal end of the second arm 108.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

The invention claimed is:

1. An implant extractor comprising:
an elongated body having a proximal end for attachment to an extraction device;
a first arm extending from the elongated body;
a second arm pivotably connected to the first arm, the second arm having a moment arm for generating a torque about a distal end of the second arm; and
a screw displacement device operatively connected to the first arm and the moment arm to apply a force to one of the first and second arms, the screw displacement device having a shaft with a longitudinal axis substantially parallel to a longitudinal axis of the elongated body.

2. An implant extractor comprising:
an elongated body;
a quick connected extending from a proximal end of the elongated body, wherein the quick connect has a longitudinal axis that extends substantially parallel to a longitudinal axis of the elongated body;
a first arm extending from the elongated body;
a second arm pivotably connected to the first arm, the second arm having a moment arm for generating a torque about a distal end of the second arm that extends substantially parallel to the longitudinal axis of the elongated body; and
a force applicator operatively connected to the first arm and the moment arm to supply a force to one of the first and second arms.

3. The implant extractor of claim 2, further comprising:
a first jaw releasably attachable to a distal end of the first arm; and
a second jaw releasably attachable to the distal end of the second arm.

* * * * *